(12) United States Patent
Follen et al.

(10) Patent No.: US 11,325,801 B2
(45) Date of Patent: May 10, 2022

(54) DISPOSABLE PRODUCT ASSEMBLY SYSTEMS AND METHODS

(71) Applicant: Curt G. Joa, Inc., Sheboygan Falls, WI (US)

(72) Inventors: Sean P. Follen, Cedar Grove, WI (US); Robert E. Andrews, Falmouth, ME (US)

(73) Assignee: CURT G. JOA, INC., Sheboygan Falls, WI (US)

( * ) Notice: Subject to any disclaimer, the term of this patent is extended or adjusted under 35 U.S.C. 154(b) by 78 days.

(21) Appl. No.: 16/947,963

(22) Filed: Aug. 26, 2020

(65) Prior Publication Data

US 2020/0385228 A1 Dec. 10, 2020

Related U.S. Application Data

(63) Continuation of application No. 15/290,714, filed on Oct. 11, 2016, now abandoned.

(60) Provisional application No. 62/240,622, filed on Oct. 13, 2015.

(51) Int. Cl.
*B65H 19/12* (2006.01)
*A61F 13/15* (2006.01)

(52) U.S. Cl.
CPC ..... *B65H 19/123* (2013.01); *A61F 13/15804* (2013.01); *B65H 2301/41702* (2013.01); *B65H 2301/41704* (2013.01); *B65H 2301/522* (2013.01); *B65H 2405/422* (2013.01); *B65H 2408/241* (2013.01); *B65H 2555/32* (2013.01); *B65H 2801/57* (2013.01)

(58) Field of Classification Search
None
See application file for complete search history.

(56) References Cited

U.S. PATENT DOCUMENTS

| | | | |
|---|---|---|---|
| 1,610,713 A | 12/1926 | Scott |
| 1,613,963 A | 1/1927 | Scott |
| 1,732,740 A | 10/1929 | Cline |
| 1,757,935 A | 5/1930 | Maas |
| 1,780,469 A | 11/1930 | Dinsmoor |
| 2,047,769 A | 7/1936 | Cullen et al. |
| 2,097,998 A | 11/1937 | Dickhaut et al. |
| 2,671,495 A | 3/1954 | Iredell et al. |
| 2,695,025 A | 11/1954 | Andrews |
| 2,769,600 A | 11/1956 | Kwitek et al. |
| 2,918,105 A | 12/1959 | Harris |
| 3,289,552 A | 12/1966 | Corazzo |
| 3,326,487 A | 6/1967 | Huck |

(Continued)

FOREIGN PATENT DOCUMENTS

| | | | |
|---|---|---|---|
| JP | S465453 Y1 | 2/1971 |
| JP | H09136751 A | 5/1997 |

(Continued)

*Primary Examiner* — Carlos R Ortiz Rodriguez
(74) *Attorney, Agent, or Firm* — Klintworth & Rozenblat IP LLP

(57) ABSTRACT

A machine for producing disposable products anticipates when a current run of a product size is coming to an end, and therefore begins loading of material rolls intended for the next product size or code that will be run. An integrated production facility layout automatically orders and stocks raw material based on production plans, and commands a production machine to produce specific products of differing configurations, and automatically loads appropriately sized raw materials into the process.

21 Claims, 18 Drawing Sheets

(56) References Cited

U.S. PATENT DOCUMENTS

| | | |
|---|---|---|
| 3,460,775 A | 8/1969 | Ford et al. |
| 3,655,143 A | 4/1972 | Wallis |
| 3,740,296 A | 6/1973 | McDonald |
| 3,783,782 A | 1/1974 | Hardt |
| 3,796,388 A | 3/1974 | Davis |
| 3,810,344 A | 5/1974 | Evans et al. |
| 3,836,089 A | 9/1974 | Riemersma |
| 3,892,012 A | 7/1975 | Keferstein |
| 3,971,524 A | 7/1976 | Nudinger et al. |
| 4,082,599 A | 4/1978 | Kozima |
| 4,103,595 A | 8/1978 | Corse |
| 4,141,193 A | 2/1979 | Joa |
| 4,307,800 A | 12/1981 | Joa |
| 4,316,756 A | 2/1982 | Wilson |
| 4,331,418 A | 5/1982 | Klebe |
| 4,411,721 A | 10/1983 | Wishart |
| 4,528,798 A | 7/1985 | Meier |
| 4,544,109 A | 10/1985 | Andreasson |
| 4,587,790 A | 5/1986 | Muller |
| 4,687,153 A | 8/1987 | McNeil |
| 4,707,970 A | 11/1987 | Labombarde et al. |
| 4,726,725 A | 2/1988 | Baker et al. |
| 4,840,609 A | 6/1989 | Jones et al. |
| 4,873,813 A | 10/1989 | Labombarde et al. |
| 4,909,697 A | 3/1990 | Bernard, II et al. |
| 4,947,536 A | 8/1990 | Suzuki et al. |
| 4,987,940 A | 1/1991 | Straub et al. |
| 5,007,522 A | 4/1991 | Focke et al. |
| 5,212,002 A | 5/1993 | Madrzak et al. |
| 5,219,127 A | 6/1993 | Boldrini et al. |
| 5,383,988 A | 1/1995 | Herrmann et al. |
| 5,472,153 A | 12/1995 | Crowley et al. |
| 5,513,936 A | 5/1996 | Dean |
| 5,556,246 A | 9/1996 | Broshi |
| 5,582,497 A | 12/1996 | Noguchi |
| 5,855,037 A | 1/1999 | Wieloch et al. |
| 5,868,899 A | 2/1999 | Gundersen |
| 5,881,964 A | 3/1999 | Fujikura et al. |
| 5,897,291 A | 4/1999 | Gerwe et al. |
| 6,050,517 A | 4/2000 | Dobrescu et al. |
| 6,062,794 A | 5/2000 | Shiba |
| 6,216,975 B1 | 4/2001 | Schaub |
| 6,217,274 B1 | 4/2001 | Svyatsky et al. |
| 6,264,133 B1 | 7/2001 | Herrmann |
| 6,264,784 B1 | 7/2001 | Menard et al. |
| 6,369,291 B1 | 4/2002 | Uchimoto et al. |
| 6,394,384 B1 | 5/2002 | Alday et al. |
| 6,451,145 B1 | 9/2002 | Forbes |
| 6,547,909 B1 | 4/2003 | Butterworth |
| 6,637,583 B1 | 10/2003 | Andersson |
| 6,685,130 B2 | 2/2004 | Stauber et al. |
| 6,701,992 B1 | 3/2004 | Pasquale et al. |
| 6,852,186 B1 | 2/2005 | Matsuda et al. |
| 6,978,964 B2 | 12/2005 | Beccari |
| 7,017,820 B1 | 3/2006 | Brunner |
| 7,214,174 B2 | 5/2007 | Mien et al. |
| 7,350,740 B2 | 4/2008 | Benvenuti et al. |
| 7,441,579 B2 | 10/2008 | Mami |
| 8,261,802 B2 | 9/2012 | Aono |
| 9,566,193 B2 | 2/2017 | Andrews et al. |
| 2001/0013561 A1 | 8/2001 | Wild et al. |
| 2003/0150909 A1 | 8/2003 | Markham et al. |
| 2004/0228709 A1 | 11/2004 | Ueda |
| 2005/0077415 A1 | 4/2005 | Hikita |
| 2005/0077416 A1 | 4/2005 | Heikaus |
| 2005/0077418 A1 | 4/2005 | Werner et al. |
| 2005/0139713 A1 | 6/2005 | Weber et al. |
| 2005/0257881 A1 | 11/2005 | Coose et al. |
| 2006/0099055 A1 | 5/2006 | Stefani |
| 2006/0222479 A1 | 10/2006 | Shiwaku et al. |
| 2007/0044895 A1 | 3/2007 | Nawano et al. |
| 2007/0131343 A1 | 6/2007 | Nordang |
| 2007/0131817 A1 | 6/2007 | Fromm et al. |
| 2007/0140817 A1 | 6/2007 | Hansl |
| 2007/0204950 A1 | 9/2007 | Tonohara |
| 2011/0033270 A1 | 2/2011 | Toncelli |
| 2011/0041997 A1 | 2/2011 | Benner et al. |
| 2011/0046772 A1 | 2/2011 | Healey et al. |
| 2012/0159753 A1 | 6/2012 | Andrews et al. |
| 2013/0056576 A1 | 3/2013 | Andrews et al. |
| 2016/0060060 A1 | 3/2016 | Macura et al. |
| 2017/0101281 A1 | 4/2017 | Follen et al. |

FOREIGN PATENT DOCUMENTS

| | | |
|---|---|---|
| JP | 2002032112 A | 1/2002 |
| JP | 2002308485 A | 10/2002 |
| JP | 2014508627 A | 4/2014 |
| JP | 2015519115 A | 7/2015 |

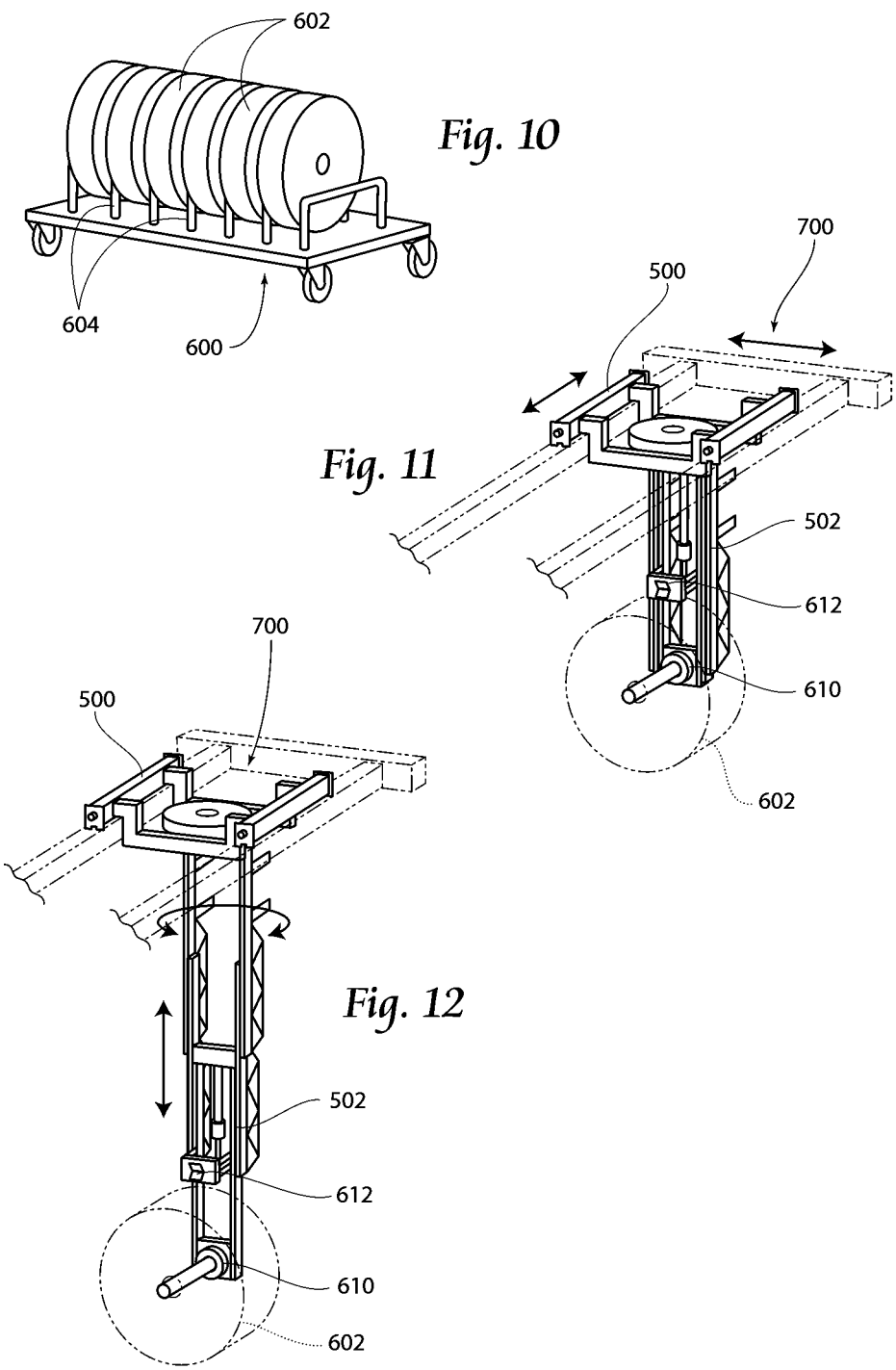

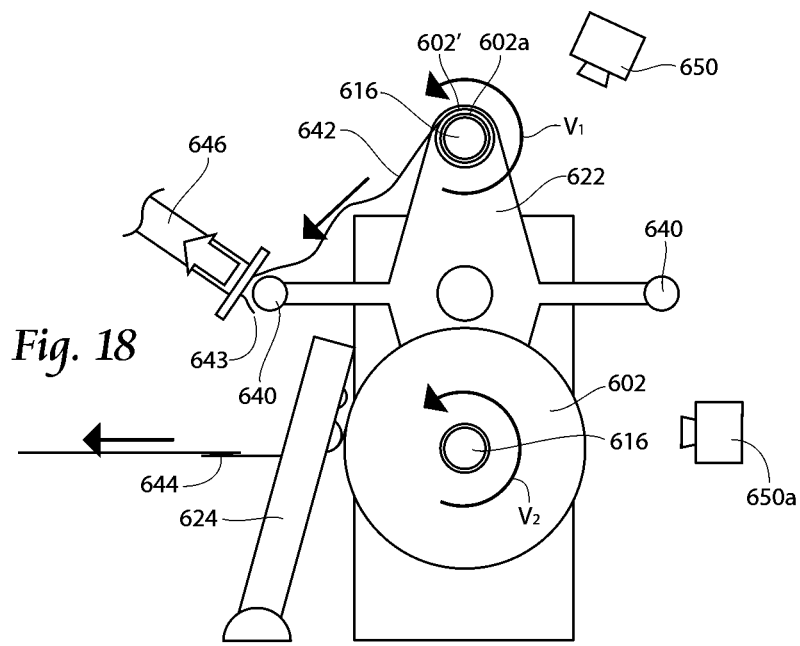
*Fig. 18*
*Fig. 18A*
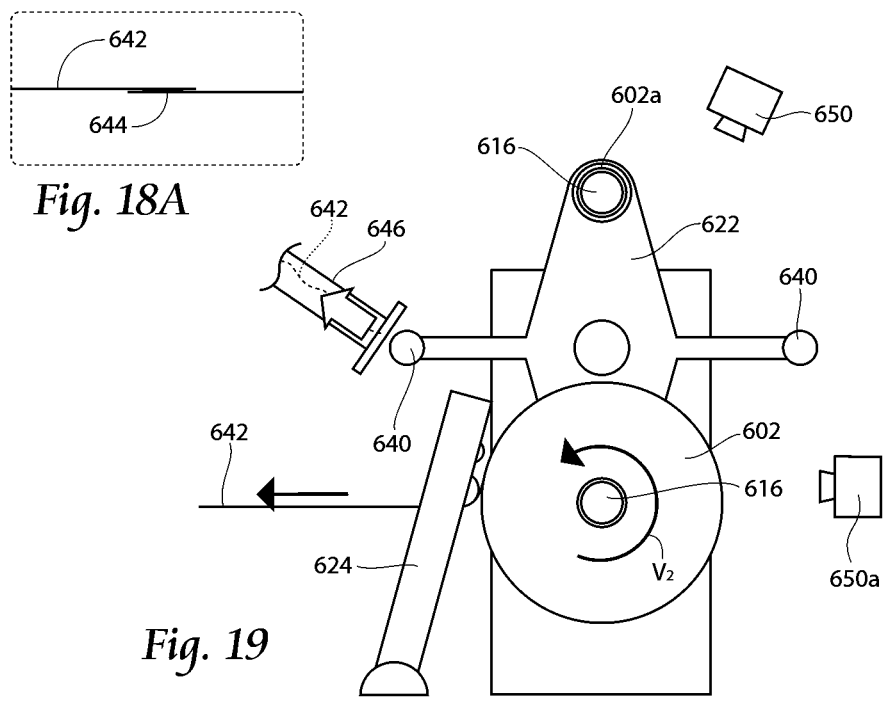
*Fig. 19*

DISPOSABLE PRODUCT ASSEMBLY SYSTEMS AND METHODS

CROSS-REFERENCE TO RELATED APPLICATIONS

The present invention is a continuation of and claims priority to U.S. patent application Ser. No. 15/290,714 filed Oct. 11, 2016, which claims priority to U.S. Provisional Patent Application Ser. No. 62/240,622, filed Oct. 13, 2015, the disclosures of which are incorporated herein by reference in their entirety.

BACKGROUND OF THE INVENTION

The invention disclosed herein relates to an apparatus and methods for forming disposable products such as diapers at very high speeds, while automatically scheduling certain aspects of production, including material loading, splicing, reloading. While the description provided relates to diaper manufacturing, the apparatus and method are easily adaptable to other applications.

In particular, the present invention relates to material unwind systems. Turret unwind systems, which automatically splice an expiring roll of material with a waiting roll of material are disclosed, the turret unwind systems provided with a recovery system for recovering end portions of the material carried by the expiring roll, and automatically separating an expiring roll core from the expiring material. Two waste streams are created—each of a single material, making recycling and downstream handling of the expiring roll cores and expiring material simpler and more efficient.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in continuously fed fashion.

In the creation of a diaper, multiple roll-fed web processes are typically utilized. To create an absorbent insert, the cellulose pulp is unwound from the provided raw material roll and de-bonded by a pulp mill. Discrete pulp cores are created using a vacuum forming assembly and placed on a continuous tissue web. Optionally, super-absorbent powder may be added to the pulp core. The tissue web is wrapped around the pulp core. The wrapped core is debulked by proceeding through a calendar unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition layer web material and a nonwoven web material, both of which are fed from material parent rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a profiled die roller and a smooth platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented, such as disclosed in related U.S. Application No. 61/426,891, owned by the assignee of the present invention and incorporated herein by reference. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splices and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slitting is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners. This is also done with turn bars upon entrance to the process.

After the nonwoven web is slit, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

In diapers it is preferable to contain elastics around the leg region in a cuff to contain exudates for securely within the diaper. Typically, strands of elastic are held by a nonwoven layer that is folded over itself and contains the elastics within the overlap of the nonwoven material. The nonwoven is typically folded by use of a plow system which captures the elastics within a pocket, which is then sealed to ensure that the elastics remain in the cuff.

Most products require some longitudinal folding. It can be combined with elastic strands to make a cuff. It can be used to overwrap a stiff edge to soften the feel of the product. It can also be used to convert the final product into a smaller form to improve the packaging.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

Roll-fed web processes typically use splicers and accumulators to assist in providing continuous webs during web processing operations. A first web is fed from a supply wheel (the expiring roll) into the manufacturing process. As the material from the expiring roll is depleted, it is necessary to splice the leading edge of a second web from a standby roll to the first web on the expiring roll in a manner that will not cause interruption of the web supply to a web consuming or utilizing device.

In a splicing system, a web accumulation dancer system may be employed, in which an accumulator collects a substantial length of the first web. By using an accumulator, the material being fed into the process can continue, yet the trailing end of the material can be stopped or slowed for a short time interval so that it can be spliced to leading edge of the new supply roll. The leading portion of the expiring roll remains supplied continuously to the web-utilizing device. The accumulator continues to feed the web utilization process while the expiring roll is stopped and the new web on a standby roll can be spliced to the end of the expiring roll.

In this manner, the device has a constant web supply being paid out from the accumulator, while the stopped web material in the accumulator can be spliced to the standby roll. Examples of web accumulators include that disclosed in U.S. patent application Ser. No. 11/110,616, which is commonly owned by the assignee of the present application, and incorporated herein by reference.

As in many manufacturing operations, waste minimization is a goal in web processing applications, as products having spliced raw materials cannot be sold to consumers. Indeed, due to the rate at which web processing machines run, even minimal waste can cause inefficiencies of scale. In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, the art of web processing would benefit from systems and methods that identify potentially defective product prior to product assembly, thereby eliminating effort during recyclable material harvesting.

Furthermore, to improve quality and production levels by eliminating some potentially defective product, the art of web processing would benefit from systems and methods that ensure higher product yield and less machine downtime.

Some diaper forming techniques are disclosed in co-pending U.S. application Ser. No. 12/925,033 which is incorporated herein by reference. As described therein, a process wherein a rotary knife or die, with one or more cutting edges, turns against and in coordination with a corresponding cylinder to create preferably trapezoidal ears. Ear material is slit into two lanes, one for a left side of a diaper and the other for a right side of a diaper. Fastening tapes are applied to both the right and the left ear webs. The ear material is then die cut with a nested pattern on a synchronized vacuum anvil.

The resulting discrete ear pieces however, due to the trapezoidal pattern of the ears, alternate between a correct orientation and an incorrect (reversed) orientation. The reversed ear is required to be rotated 180° into the correct orientation such that the ears and associated tape present a left ear and a right ear on the diaper.

To accomplish the reversal of the ear pattern, discrete ear pieces are picked up at the nested ear pitch by an ear turner assembly that will expand to a pitch large enough for ears to be unnested and allow clearance for every other ear to be rotated. The rotated ears are then unnested and into the correct orientation.

Two ear turner assemblies can be provided, to rotate every other ear applied to the right side of the product, and every other ear applied to the left side of the product. In this manner, for a single product, one of the two ears will have been rotated 180°.

Ear application to a chassis web can be by a bump method (described later) with intermittent adhesive applied to the chassis web, or can be by vacuum transfer.

The present invention also allows for two side panel assemblies, including fastening mechanisms, to be attached to two ears, the side panel assemblies attached in a pre-folded condition. Two more ears can be coupled to a chassis web to create a front panel to wear about the waist of a user.

The present invention also allows for chips of material to be removed from the ears to provide a diaper with contoured leg openings. In one embodiment, the chips may be removed from the ears before the ears are attached to the chassis web. In an additional embodiment the chips may be removed from the ears after the ears are attached to the chassis web. In an additional embodiment the chips may be removed from the ears and a portion of the chassis web removed after the ears are attached to the chassis web.

The invention disclosed herein also relates to apparatus and methods for waste reduction, such as disclosed in related U.S. Application Ser. No. 61/400,318, also incorporated herein by reference. Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion. As in many manufacturing operations, waste minimization is a goal in web processing applications, as products having spliced raw materials cannot be sold to consumers. Indeed, due to the rate at which web processing machines run, even minimal waste can cause inefficiencies of scale.

In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, it is beneficial to use up all of incoming rolls, so that a portion of the incoming rolls do not become waste. That objective is accomplished with the present invention.

When manufacturing hygiene products, such as baby diapers, adult diapers, disposable undergarments, incontinence devices, sanitary napkins and the like, a common method of applying discrete pieces of one web to another is by use of a slip-and-cut applicator. A slip-and-cut applicator is typically comprised of a cylindrical rotating vacuum anvil, a rotating knife roll, and a transfer device. In typical applications, an incoming web is fed at a relatively low speed along the vacuum face of the rotating anvil, which is moving at a relatively higher surface speed and upon which the incoming web is allowed to "slip". A knife-edge, mounted on the rotating knife roll, cuts off a segment of the incoming web against the anvil face. This knife-edge is preferably moving at a surface velocity similar to that of the anvil's surface. Once cut, the web segment is held by vacuum drawn through holes on the anvil's face as it is carried at the anvil's speed downstream to the transfer point where the web segment is transferred to the traveling web.

Continual improvements and competitive pressures have incrementally increased the operational speeds of disposable diaper converters. As speeds increased, the mechanical integrity and operational capabilities of the applicators had to be improved accordingly.

Decreasing the footprint required by the manufacturing equipment is also desirable, as is increased automation, decreased system downtime, and increased manufacturing speeds. In typical disposable products manufacturing techniques, raw materials are fed into the manufacturing system at ground level, generally from the sides (and often perpendicular on the ground level) relative to the main machine direction on the ground.

The raw material supply system can also be done manually. A forklift operator is typically required to constantly monitor supplies of raw materials, such as the nonwoven materials, elastics, pulp, SAP, tape, poly, etc. and drive the forklift from a storage area containing these materials, and deposit those materials onto the system, where typically splicing systems are used to provide for continuous operation. In prior art systems, an operator would typically use a utility knife to slice layers of web material remaining on an almost empty core, in order to separate the core from the remaining web material carried by the core. By using an automated material supply system, along with a system described in U.S. Application No. 62/206,394, there is no longer a need for manual separation of the last layers of web material from the core.

SUMMARY OF THE INVENTION

Provided are methods and apparatus for minimizing waste and improving quality and production in web processing operations in a high speed, small footprint environment.

Disclosed is an Automatic Roll Loading System (ARLS). Specifically, the machine of the present invention anticipates when a current run of a product size is coming to an end, and therefore begins loading of material rolls intended for the next product size or code that will be run.

Once all material unwinds have the size of material rolls loaded and splices set up, splices can by manually or automatically triggered to splice in the new material rolls and use the running machine process to pull all the new materials through the process. This saves considerable time compared to loading each unwind manually and then manually rethreading each material process throughout the machine. The result is a significant reduction in changeover times and the present technique can be employed for any machine process requiring input of multiple material rolls when different materials (size, weight, color, etc.) are required for different products codes or sizes.

When employing the technique described herein, splicing in different width materials and pulling them through a running machine process will not result in the immediate making of acceptable products. The present method results in intentionally pulling in material widths different than what the current product code being run is setup for, so certain details will result in unacceptable product; for instance, glue applicator patterns may exceed the new material width and therefore glue applicators are turned off for the duration of this material pull through technique. For the same reason, web with detectors are temporarily disable or ignored, and web guides put into a non-responsive mode so they do not try and respond to material widths not compatible with their current setup. Those machine capabilities are restored prior to starting the next good product run, but by pulling in new materials through web processes by using the old materials already threaded through web processes, good-product to good-product changeover is greatly sped.

An ARLS Scheduler monitors machine speed, consumption of raw materials, materials remaining on each turret unwind, progress on case count of current product code run, schedule of next product code run, materials available at machine, materials remaining on each material loading cart, and optionally, materials in warehouse, and general position of robot carts in motion.

First, the ARLS Scheduler determines which turret unwind should be loaded next. It also determines when material rolls specific to the NEXT product code to be run should be loaded onto the associated turret unwinds. This is part of the preparation to conduct the special splice event as part of the current product code run shutdown. Once new materials are pulled through the machine process (auto-threaded) by the expiring materials, the machine can be full shut down in preparation for other, non-material related changeover activities to set the machine up for the next product code run.

The ARLS Scheduler may also keep track of the changeover parts, assemblies, and set-ups needed for each specific changeover to assist the machine operators and technicians in their outside time preparations for the changeover as well as during the inside time changeover activities when in progress.

The basic roll loading decision is informed by information queries such as: material remaining on each cart; status of a turret unwind as ready to load; and the time remaining or product pitches remaining to end of roll on the turret unwind. The decision could be located in the turret unwind control routine, the ARLS PLC, or the machine control PLC depending on size, complexity, or configuration of machine.

A vertical reciprocating conveyor or a robot is used to carry waiting new material rolls from a main processing level to the material unwinding level. A robotic assembly obtains an expiring roll and discards the roll in a waste chute. Once on the material unwinding level, the waiting new material rolls are staged at a material address dedicated to that particular material. A robotic assembly acquires a material roll from one of said material addresses and transports and places the material roll onto its appropriate auto-fed material unwinding system.

Turret unwind systems, which automatically splice an expiring roll of material with a waiting roll of material are disclosed, the turret unwind systems provided with a recovery system for recovering end portions of the material carried by the expiring roll, and automatically separating an expiring roll core from the expiring material. Two waste streams are created—each of a single material, making recycling and downstream handling of the expiring roll cores and expiring material simpler and more efficient.

The material supply techniques and product layouts disclosed can be used to produce pant-type diapers, brief-type diapers, baby diapers, adult diapers, or any other types of disposable products using web processing machinery.

A system for manufacturing disposable products is disclosed, the system comprising a production machine for producing a first configuration of disposable products and a second configuration of disposable products; a first set of material rolls configured to produce said first configuration of disposable products; a second set of material rolls configured to produce said second configuration of disposable products; a controller communicatively coupled to said production machine, said controller receiving a plurality of input signals, and, based upon said input signals, generating an output signal controlling whether said first configuration or said second configuration of disposable products is produced by said production machine; said controller selectively coupling at least one of said first set of material rolls and said second set of material rolls with said production machine based upon at least one of said input and output signals, to selectively produce said first and said second configurations of disposable products.

Input signals can comprise at least one of scheduling input, sales and marketing input, purchasing input, receiving input, warehousing input, production input, maintenance input, shipping input, and accounting input, and based on those inputs, arrive at an output decision. In a preferred embodiment, the scheduling input is reactive to at least one of sales and marketing input and purchasing input.

The system is capable of producing different disposable products, for instance by supplying new material rolls having a first roll width, and said second set of material rolls comprising a plurality of new material rolls having a second roll width, said second roll width larger than said first roll width. In this manner, the disposable products themselves can be characterized as having a first product width, said second configuration of disposable products comprising disposable products having a second product width, said second product width larger than said first product width.

BRIEF DESCRIPTION OF THE DRAWINGS

FIG. 10 is a perspective view of a loaded material roll supply cart of the present invention;

FIG. 11 is a perspective view of a gantry crane system carrying a material roll used in the present invention, shown in a retracted position;

FIG. 12 is a perspective view of a gantry crane system carrying a material roll used in the present invention, shown in an extended position;

FIGS. 14-22 are views of a splicing and material recovery sequence.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

It is noted that the present waste minimization techniques and apparatus are described herein with respect to products such as diapers, but as previously mentioned, can be applied to a wide variety of processes in which discrete components are applied sequentially.

Figure 1A:
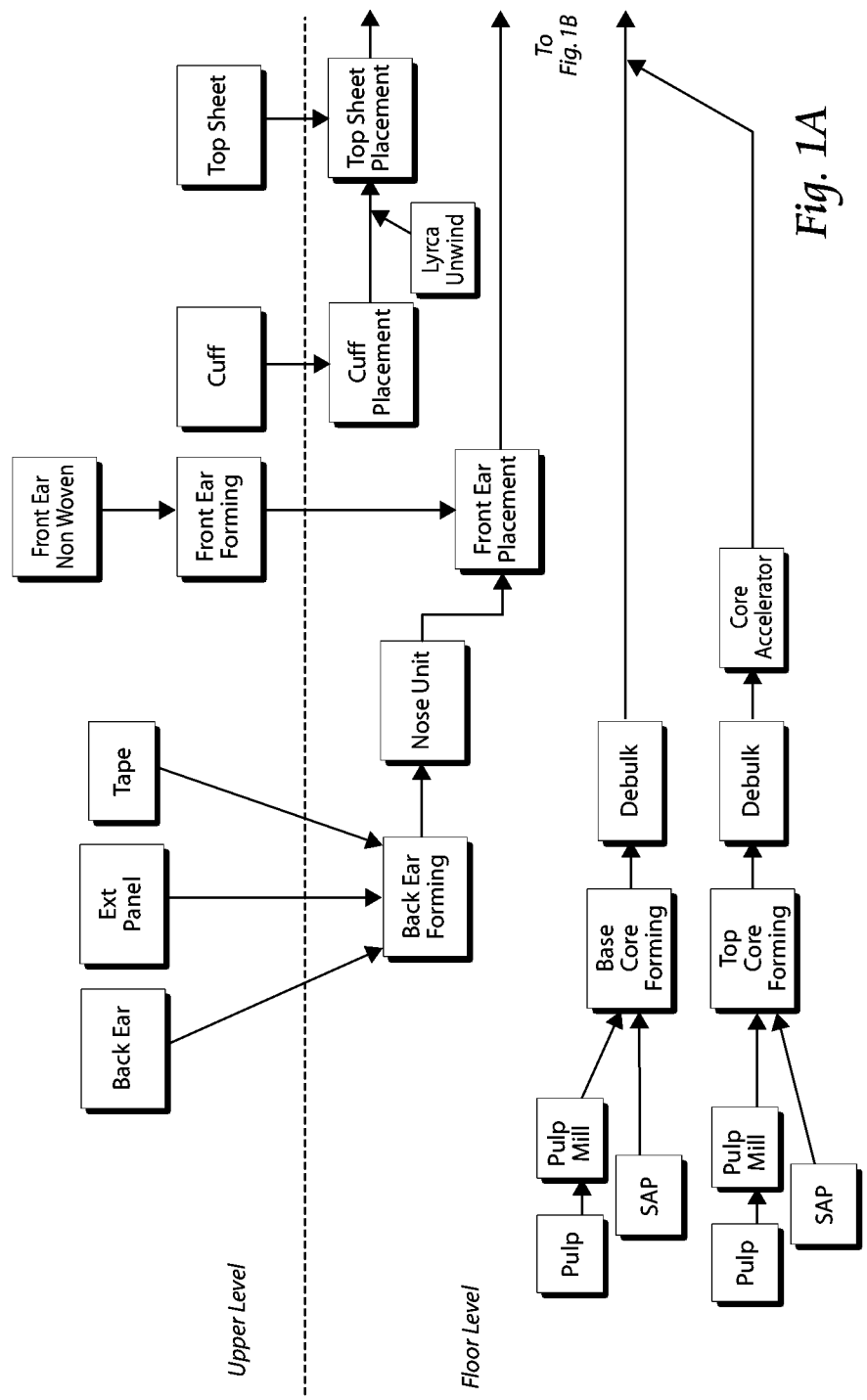
FIGS. 1A and 1B are a schematic of a representative web processing system.
Figure 1B:
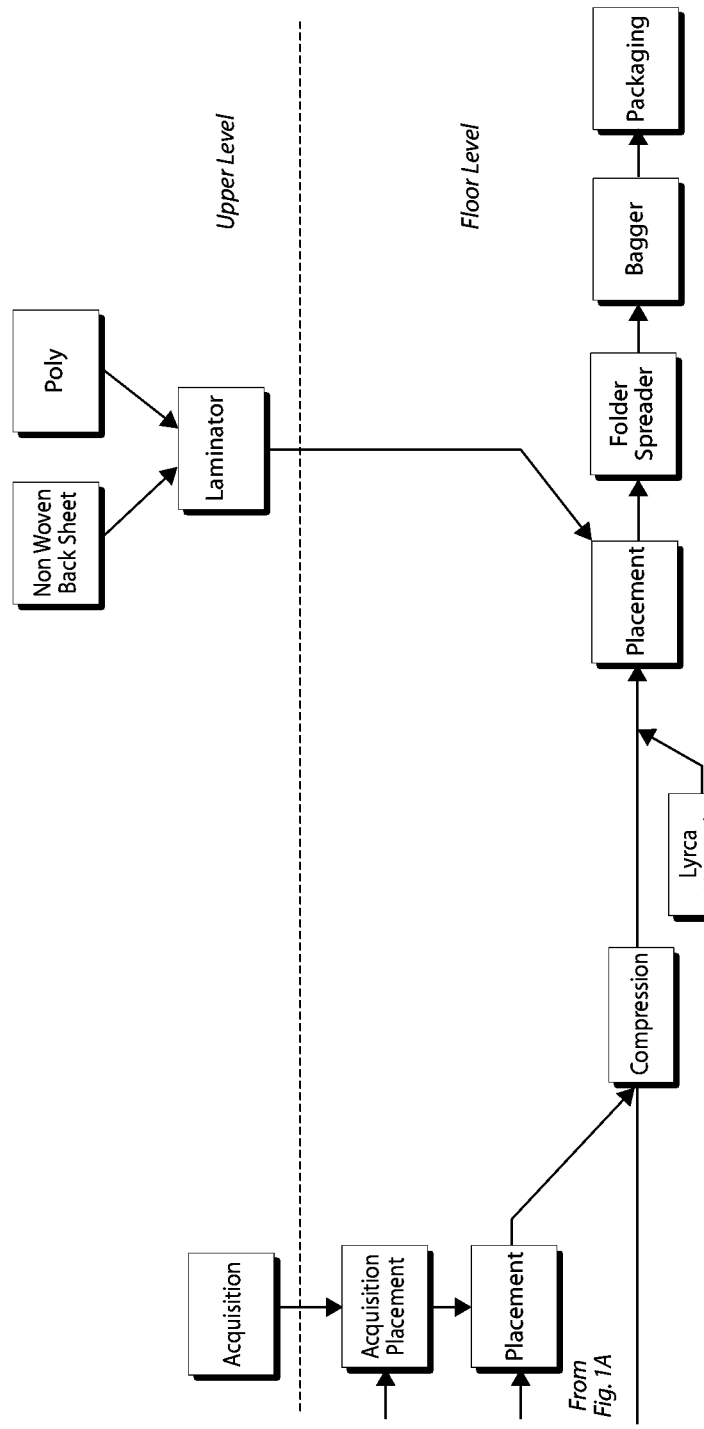

Referring to FIGS. 1A and 1B, a two-level disposable product manufacturing process is disclosed. Portions of the disposable product are formed on a floor level, and other portions are formed on an upper or mezzanine level.

On the floor level, the web processing operation starts with incorporating raw materials such as paper pulp and super absorbent polymer (SAP) in a pulp mill. The mixture is sent to a core forming drum, where cores are formed for retaining liquids. A core can be placed on a tissue and processed as shown. Eventually, an additional tissue layer can be applied to sandwich the core. In the illustrated embodiment, two independent cores can be formed and joined together at a compression unit.

Simultaneously formed on the upper level are back ear and front ear portions of the disposable product, which can be formed with methods and apparatus such as those disclosed in the simultaneously pending U.S. patent application Ser. No. 12/925,033, incorporated herein by reference, and described in the schematic as the "NOSE unit."

As disclosed therein, discrete preferably trapezoidal ear pieces are initially cut alternating between a correct orientation and an incorrect (reversed) orientation. The reversed ear is required to be rotated 180° into the correct orientation such that the ears and associated tape present a left ear and a right ear on the diaper.

To accomplish the reversal of the ear pattern, discrete ear pieces are picked up at the nested ear pitch by an ear turner assembly that will expand to a pitch large enough for ears to be unnested and allow clearance for every other ear to be rotated. The rotated ears are then unnested and into the correct orientation.

Two ear turner assemblies can be provided, to rotate every other ear applied to the right side of the product, and every other ear applied to the left side of the product. In this manner, for a single product, one of the two ears will have been rotated 180°.

Ear application to a chassis web can be by a bump method with intermittent adhesive applied to the chassis web, or can be by vacuum transfer.

Still on the upper level, a cuff portion of the diaper can be supplied from the upper level, the top sheet can be stored and unwound, an acquisition layer can be stored and unwound, and a nonwoven backsheet/poly laminate can be stored, formed and unwound. All of the stored materials on the upper level can be retrieved automatically and mechanically to restock as the rolls are used up. Eventually the upper level materials, which generally overlay the floor level machinery, are supplied down to the floor level for use in the diaper manufacturing process.

Together on the floor level, the back ear, front ear, cuff (now including cuff elastic), top sheet, acquisition layer, and backsheet/poly laminate are preferably simultaneously placed and coupled together and coupled with the previously formed core. The web can undergo folding, extraction and trimming of excess material, and application of material to tighten the diaper about the waist. Eventually, the product is folded and packaged.

Figure 2:
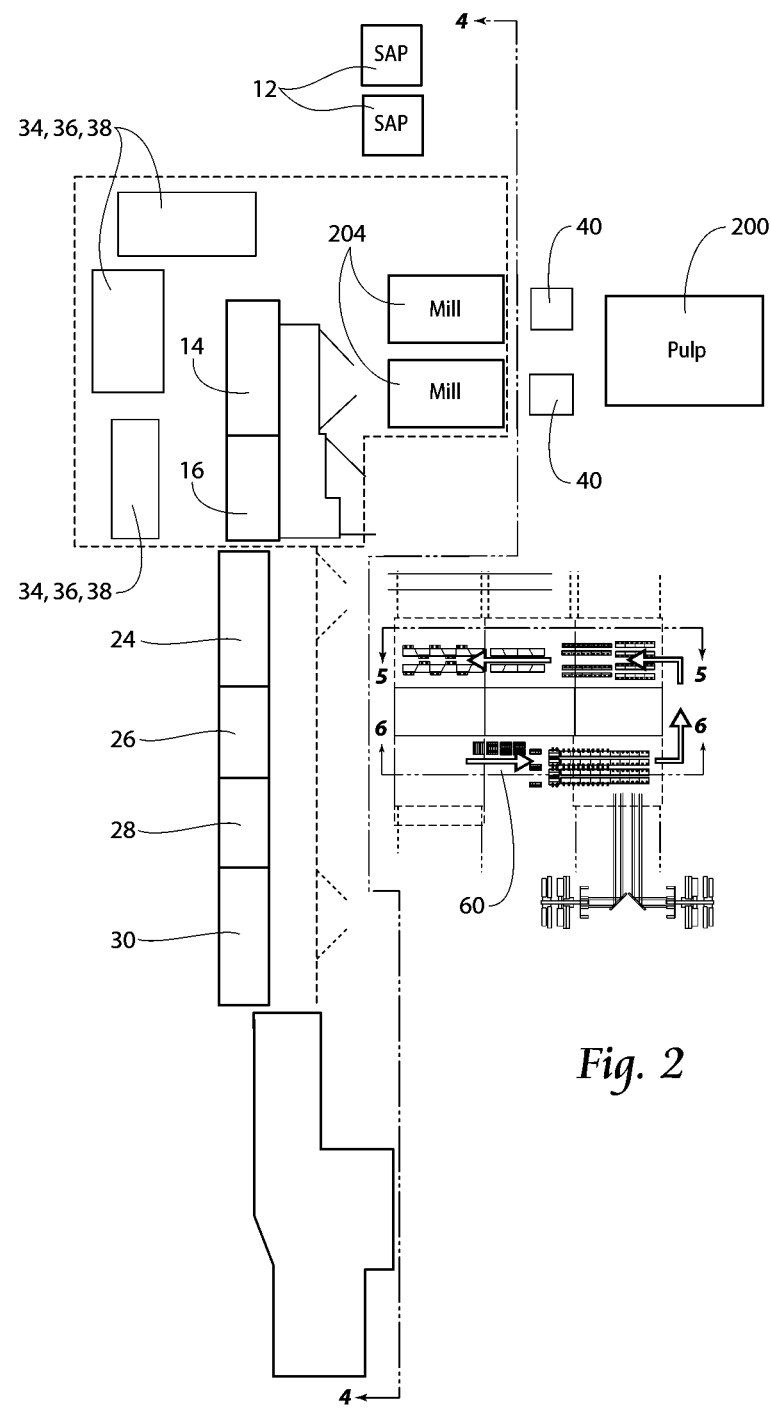
FIG. 2 is a top view of a floorplan layout of the web processing system of the present invention.
Figure 4:
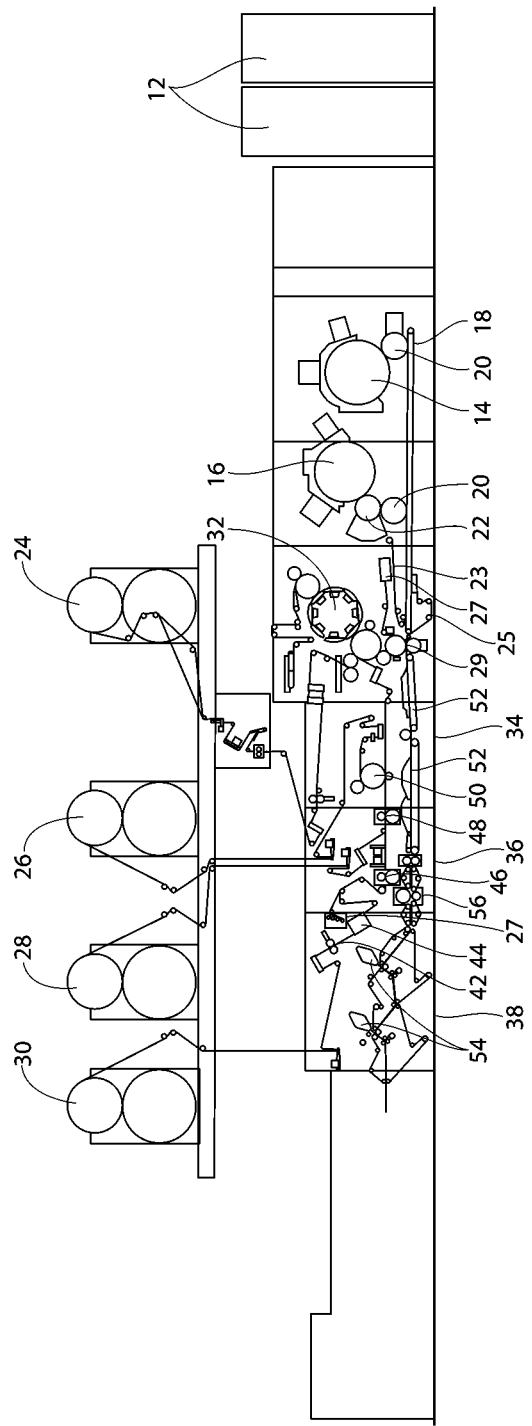
FIG. 4 is a side view of the ground level and mezzanine levels of the web processing system of the present invention.

Referring now to FIGS. 2 and 4, a preferred floor plan of the present invention is shown both from a top view (FIG. 2) and a side view (FIG. 4). As indicated, pulp rolls 200 feed raw pulp into a pulp mill 204, where the pulp is de-bonded. Super absorbent polymer is added from station 12. The SAP/pulp mixture, or pulp/SAP blend, or pulp and SAP is fed onto core forming drum 14. The pulp/SAP mixture is introduced to a core forming apparatus. Cores are made by conveying the pulp/SAP mixture through a duct and into a vacuum forming drum. Cores from core forming drum 14 are conveyed by conveyor 18 and core accelerator 20 downline. A secondary core forming drum 16 is likewise employed if a secondary core is desired, and the secondary core is passed through the debulking unit 22, and onto the core accelerator 20 and placed atop the primary core. A compression conveyor 23 keeps control of the core to pass it through to the introduction of poly laminate backsheet. A backsheet laminate is comprised preferably of a continuous nonwoven layer (for soft, cloth like feel), along with a moisture barrier layer, generally made from polypropylene or polyethylene film. This layer can be glued, ultrasonically bonded over the length of the backsheet, or applied as a patch with glue using a slip/cut process.

Figure 3:
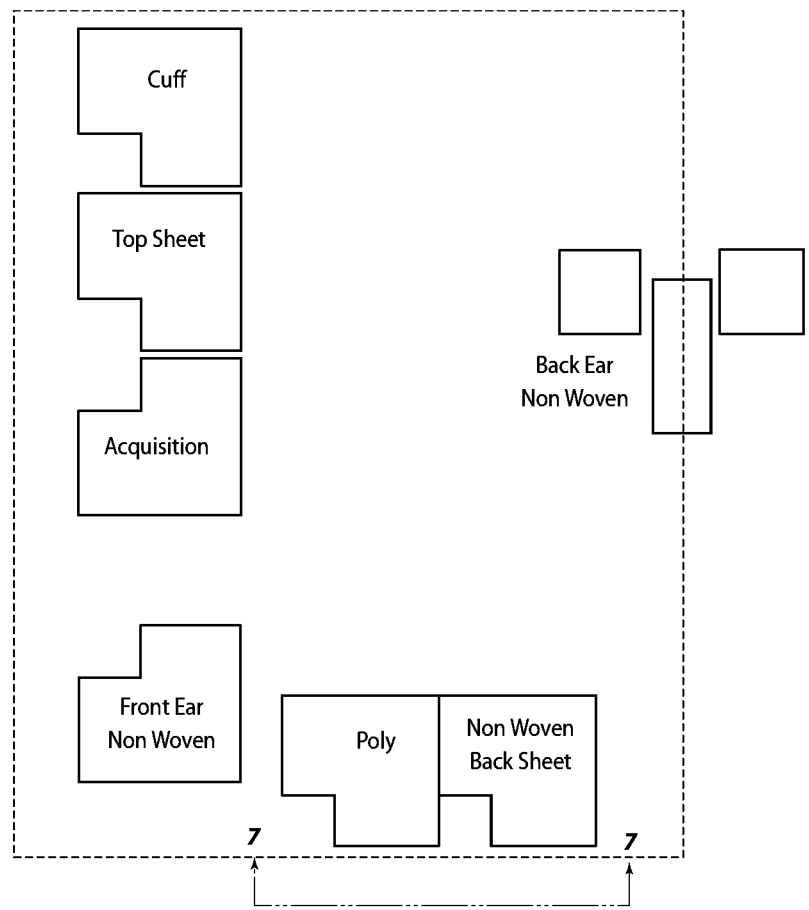
FIG. 3 is a top view of a floorplan layout of the web processing system of the present invention.
Figure 7:
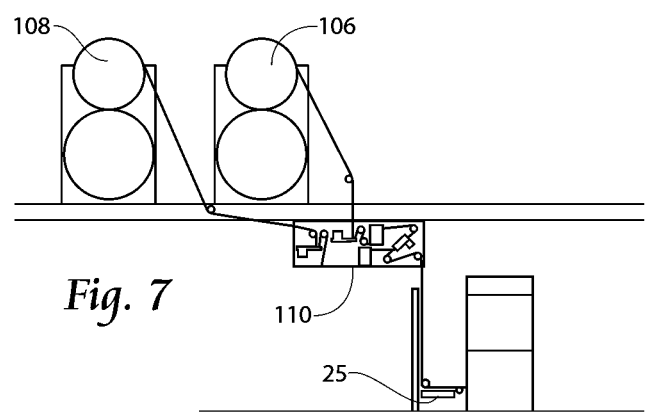
FIG. 7 is a side view of a soft backsheet lamination section of the present invention.

Referring to FIG. 7, the formation of the soft backsheet lamination is shown in side view. A nonwoven backsheet roll is carried on the upper level along with its backup roll to be spliced in as inventories deplete (see FIG. 3) and laminated together at station 110.

Referring to FIGS. 4 and 7, it can be seen that a process interface module 110 is carried between said unwind level and said main processing level, said main level containing splice preparation equipment 110 located between the unwind level and the main process system level, for instance by hanging a process interface module 110 from a supplied I-beam. The process interface module can achieve many functions, such as slitting, laminating, and splice preparation. After being transported vertically, the poly laminated backsheet is introduced to the fed from the bottom, at station 25 (see FIGS. 3, 7). A nonwoven topsheet assembly, including a lycra and cuff portion and an absorbent distribution layer, enters the system prior to the boundary compression unit. Still referring to FIG. 3, it is noted that actual raw materials and the locations of those materials could vary in floor plan, but it is preferred that the materials remain on the vertical levels shown.

Referring back to FIG. 4, this poly laminate and core combination is passed to boundary compression unit 29. It is at unit 29 that other diaper elements are introduced in pre-formed fashion, from the upper level components on FIG. 1B. Also, lycra unwind unit 27 introduces lycra, in addition to the pre-formed upper level diaper components, at this point.

Referring to FIG. 2, the upper level components comprise the front ear nonwoven supply unit 24, to supply the front ears, the acquisition layer provided from unwind unit 26, the top sheet supplied from the supply and unwind station 28, and the cuff components supplied from the cuff supply unit 30 to supply the cuff material for lower level slitting/spreading and introduction of lycra, and foldover of the lycra to form the cuff. These materials are fed in the pathways shown, and introduced to the boundary compression unit 29, in the sequence shown in FIGS. 1A and 1B.

Figure 5:
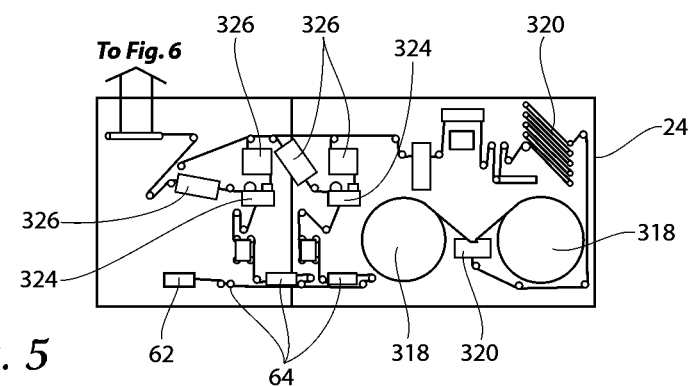
FIG. 5 is a side view of an extension panel construction section of the present invention.
Figure 6:
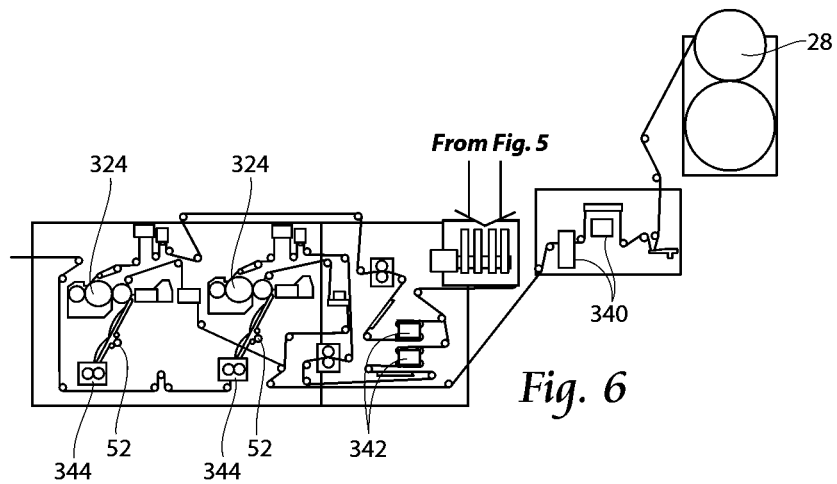
FIG. 6 is a side view of a back ear final construction section of the present invention.

Still referring to FIG. 2, on the upper level, the back ear and extension panel are formed at station 60. The back-ear section is formed as shown in FIG. 6, using the methods and apparatus formed in U.S. application Ser. No. 12/925,033, disclosed herein by reference. The extension panel section is formed as shown in FIG. 5. In particular, the depiction and description shown in FIG. 19A-26 of U.S. application Ser. No. 12/925,033 results in the back ear/extension panel formation depicted in FIGS. 5 and 6. Ultimately the back ear/extension panel construction is transported as depicted, downwards toward the nested zero waste ear rotation unit 27 as shown on FIG. 4, also described in detail in U.S. application Ser. No. 12/925,033, for instance at FIG. 8A of that application.

Still referring to FIG. 4, front ears are formed at unit 24 using preferably nonwoven material, and are placed onto the chassis web preferably by slip-cut technique after being conveyed circuitously and downwardly towards the boundary compression unit 29.

Cuff unit 30 conveys, from the upper level, cuff material to the lower level where right and left cuffs are formed by passing the cuff material first through slitter 42, spreader 44. Lycra unwind unit 27 feeds strands of lycra onto the cuff material, and then a bonding/foldover unit 46 seals the lycra strands within a foldover portion of the nonwoven material to create the cuff.

An additional bonding unit 48 couples the previously created cuff with the incoming topsheet material 28, fed from the upper level downwardly. The cuff/topsheet combination is fed toward incoming acquisition layer 26 for acquisition placement at station 50 and that combination is then fed toward the NOSE unit 32, where the previously formed materials will be joined with the cuff/topsheet/acquisition combination. After the NOSE unit, all of the materials are then joined at the boundary compression unit, including the nonwoven topsheet assembly, including an absorbent distribution layer, lycra and cuff portion, which have entered the system prior to the boundary compression unit.

Now moving right to left on FIG. 4, the formed diaper can be subjected to folding plows 52 to fold over front ear and back ear/extension panels, passed through a die cut unit 56 to sever individual products from the previously continuous web, and then past tucker blades 54 to fold the products at the crotch region or elsewhere desired for packaging and bagging operations at station 00.

Referring now to FIG. 5, the extension panel construction is shown. The formation of side panel assemblies begins with an nonwoven web material 318, supplied in primary and backup roll fashion, with splicer 320 and accumulator 322 used to provide a continuous web, which is slit and spread into discrete nonwoven web portions (see FIG. 2), each of the nonwoven web portions also preferably being cut in the cross-machine direction into the preferred size.

To each of the discrete nonwoven web portions, one or more fastening mechanisms are applied. Fastening mechanisms can be tape tabs, covered tape tabs, strips of hook and loop material, continuous hook and loop material, patches of hook and loop material, etc. The fastening mechanisms will be unfastened and refastened about the waist of the user to tighten the disposable garment about the waist.

The fastening mechanisms are supplied by incoming web 62, slit and spread by units 64 and applied via slip cut unit 324 onto the nonwoven 318.

Next, the nonwoven webs 318 carrying fastening mechanisms 322 are folded over, creating a folded web 318 and folded-over fastening mechanisms. This causes the combination of the nonwoven web 318 and the fastening mechanisms to be narrower than the discrete nonwoven web portions. It is noted that the folded fastening mechanisms of web portions 318a and 318b will have opposing fastening mechanisms 322' as they will become the right and left hip waist fastening mechanisms, respectively, once placed about the waist of a user (shown later in the process).

Referring now to FIG. 6, the back ear final construction is shown, a cross sectional view of the designated view of FIG. 2. This process is disclosed, e.g., in FIGS. 20-22 of simultaneously pending U.S. patent application Ser. No. 12/925,033, incorporated herein by reference.

The back ear final construction receives where indicated the partially completed extension panel assembly where indicated, which first pass through additional folding units 342. A back-ear web 28 is provided upon which to attach the previously formed extension panel. This too can be slit and spread into discrete stretch laminate web portions.

Next, the nonwoven web portions, including their respective fastening mechanisms, are slip/cut and bonded to stretch laminate web portions in a staggered relationship, forming the side panel assemblies in four different lanes. The nonwoven web portions can be bonded to the stretch laminate web portions in any fashion, such as by ultrasonic bonding.

The stretch laminate portions can also be folded if desired, or the stretch laminate portions in combination with the nonwoven web portions can all be folded together and again, by plows 52. The back ear/extension panel construction assembly is then conveyed to the floor level NOSE unit 32, ultimately for placement with the other components and the boundary compression unit 29.

Figure 8:
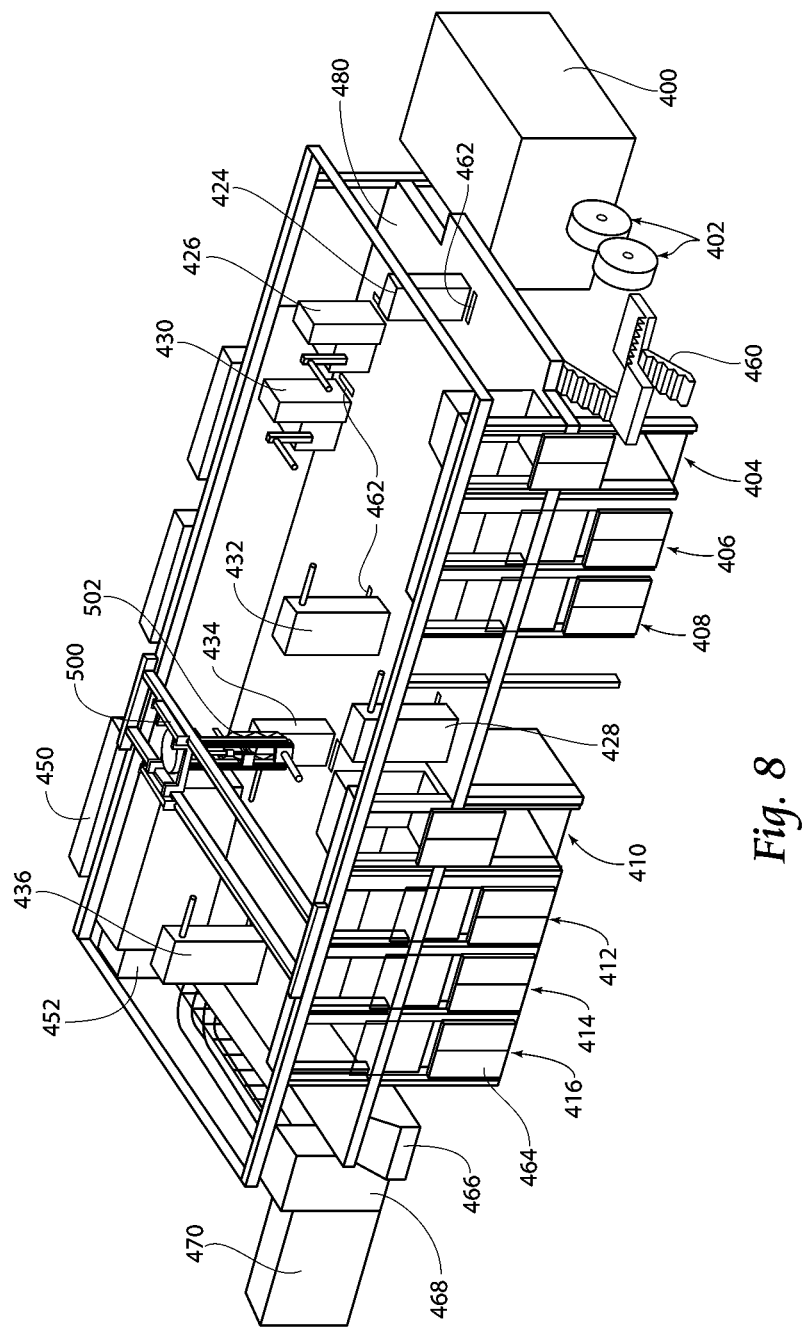
FIG. 8 is a perspective view of a mezzanine and floor level of a web processing system of the present invention used to create a pant-type product.

Referring now to FIG. 8, a perspective view of a mezzanine (or material unwinding) level 480 and floor (or main processing) level 482 of a web processing system used to create a pant-type product of the present invention is shown. The material unwinding level 480 is a human-free zone, intended for no human occupation during machine operation in areas accessible by a gantry crane 500.

On the floor level, a series of ground floor material access doors 464 are provided. These access doors 464 are each preferably dedicated to a single material. For example, in a preferred embodiment, door address 416 is for transporting inner nonwoven material from the ground level to the mezzanine level. Address 414 is for outer nonwoven, address 412 for nonwoven backsheet material, address 410 for non-woven topsheet material, address 408 for poly backsheet material, address 406 for acquisition layer material, and address 404 for tissue material. A vertical reciprocating conveyor (VRC) operates behind each access door 464 to lift a full rack of waiting new material rolls (FIG. 10) supplied into the addresses in magazines to the mezzanine level. Alternatively, descending robots can be used in place of the VRCs.

Preferably, when an access door 464 is open, a corresponding access door on the mezzanine level is closed, and vice versa.

On the material unwinding level 480, unmanned, auto-fed material unwinding systems are provided corresponding to the materials supplied to addresses above. In a preferred layout, turret unwind 424 is for a tissue unwind, corresponding to address 404 on the ground and mezzanine levels (turret unwind detail provided in FIG. 13). An acquisition layer unwind station 426 (corresponding to station 406) is provided, as are turret unwinds for poly backsheet unwind 428 (corresponding to station 408), nonwoven topsheet layer 430 (corresponding to station 410), nonwoven backsheet layer 422 (corresponding to station 412), outer chassis nonwoven unwind 434 (corresponding to station 414), and inner chassis nonwoven unwind 436 (corresponding to station 416).

As material is unwound from the unwinds 424, 426, 428, 430, 432, 434, and 436, material is fed through material supply slots 462 in the floor of the mezzanine level, downward to the ground level 482. There, the materials are fed into and used by the system, as shown in FIGS. 1A and 1B, 2, and 4-7.

As a connected material roll feeds material from the mezzanine level through an opening 462 in the floor of the mezzanine level to the floor level, the material roll will eventually expire.

During machine operation, those portions of the mezzanine level accessible by a gantry crane system 500 are designed to operate without human occupation. This not only provides an added measure of safety, but an added measure of automation for the machine. A gantry crane system 500 operates robotically on an overhead system that allows movement across a horizontal plane. The present invention uses the gantry crane 500 for horizontal movement, and a robotic arm 502 capable of vertical movement and rotation, and equipped with a camera operated location system (see FIGS. 11 and 12) to detect the position of the core of waiting new material rolls for pickup, and to deposit precisely a core of a replacement waiting new material roll onto arms of turret unwinds for use in the system.

Gantry robots 500 are preferred for this pick and place applications because of positioning accuracy, aided by vision systems. Positional programming is done in reference to an X, Y, Z coordinate system.

Although humans can access the mezzanine level 480 by stairs 460 for equipment service, no human occupation during operation is intended. Humans can also access the mezzanine level 480 behind access door 452, this portion of the mezzanine level 480 is physically separated from the human-free zone of the other portions of the mezzanine level 480. Access door 452 is used to access physically divided power station and control station 450. This station is for control panels, ultrasonic bonder control, and drive controls.

Also evident on FIG. 8 are pulp rolls 402 supplying pump mill 400 at the beginning of the processing on the main floor, and a final knife unit 466, an ear folding and horizontal pad turner 468, and lastly a cross-folder 470 which discharges the diapers to product packaging downstream.

This unique machine layout has achieved significant machine length decrease. Exemplary prior art diaper making machines for a pant process are approximately 44 meters, and this new machine layout can be achieved in less than 34 meters, a 23% shorter overall machine length from the beginning of the pulp unwind to the end of cross-folder 470. A range of 20-35% decrease in machine length can be achieved.

Figure 9:
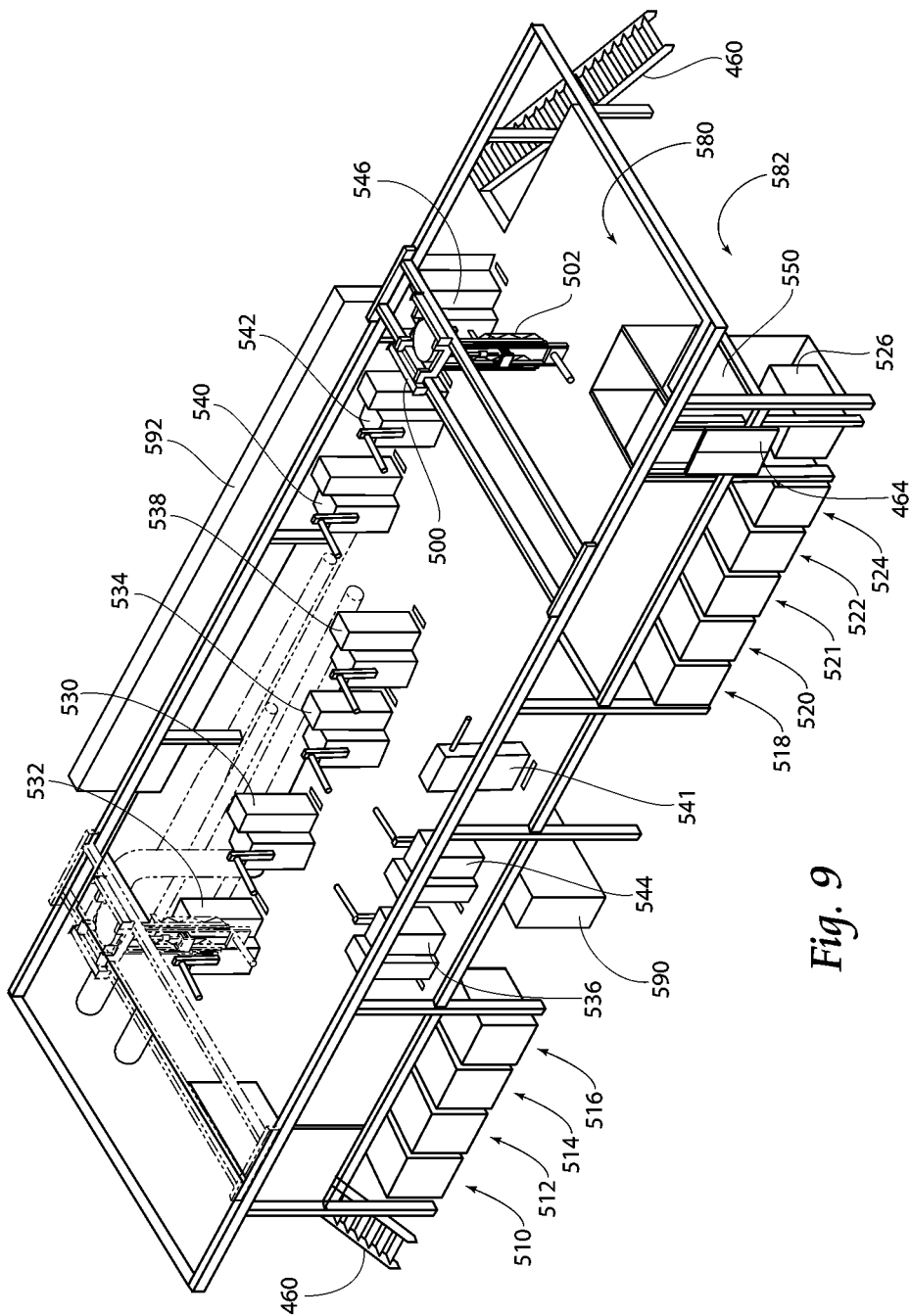
FIG. 9 is a perspective view of an alternate mezzanine and floor level of a web processing system of the present invention used to create a brief-type product.

Referring now to FIG. 9, a perspective view of an alternate mezzanine and floor level of a web processing system of the present invention used to create a brief-type product is shown.

In this embodiment, carts of materials are staged initially on the ground floor. In an exemplary embodiment, loading carts are position at stations 510 (upper tissue), 512 (lower tissue), 514 (poly backsheet), 516 (nonwoven backsheet), 518 (back ear), 520 (acquisition layer), 521 (front ear), 522 (nonwoven topsheet), 524 (extension panel), and 526 (cuff). These materials are transported to and placed behind VRC door 464 and transported by VRC 550 to the mezzanine level 480. A similar demand/replacement system is employed in the brief-type product floor layout as in the pant-type product layout described in FIG. 8. Namely, expiring materials are fed through slots in the floor of the mezzanine level, a splicing sequence is initiated, and a material replacement sequence is initiated, whereby a material roll is acquired by crane/robot combination 500/502 and transported to and placed on the turret unwind systems.

In the pictured embodiment, a lower tissue turret unwind 532 is provided as are turret unwind stations for upper tissue (530), poly backsheet (534), nonwoven backsheet (536), back ear (538), acquisition layer (540), front ear (541), inner top-sheet nonwoven extension panel (544), cuff (546). These materials are all fed downward to be used in a brief-type diaper.

This unique machine layout has achieved significant machine length decrease. Exemplary prior art diaper making machines for a brief process are approximately 41 meters, and this new machine layout can be achieved in less than 29 meters, a 30% shorter overall machine length from the beginning of the pulp unwind to the end of cross-folder 470. A range of 20-35% decrease in machine length can be achieved. A power station and control station 592 is provided. Additionally, certain components can be fed at the ground level, for instance an offline stretch material unwind 590.

Referring now to FIG. 10, a perspective view of a loaded material roll supply cart 600 or magazine of the present invention is shown. A material staging magazine 600 is provided to carry waiting new material rolls 602 from a ground level to a mezzanine level 480, the mezzanine level 480 carrying a series of turret unwind systems for dispensing materials from the mezzanine level back to the ground level. The material staging magazines 600 contain a series of individual roll stabilization features 604 which prevent waiting new material rolls 604 from tipping during material transport and unloading. The cart 600 is filled on the ground level, and rolled into the appropriate ground level addresses 404, 406, 408, 410, 412, 414, and 416, for transport to mezzanine level addresses 404, 406, 408, 410, 412, 414, and 416. The rolls are then summoned as described above.

Referring now to FIG. 11, a perspective view of a roll transfer device 700 comprising a gantry crane 500 system carrying a material roll 602 used in the present invention is shown in a retracted position. A camera 612 is used to detect the position of a core of a waiting new material roll during pickup of a waiting new material roll by the robot off of a cart 600, and also to detect the position of the shaft 616 on the turret unwind systems (FIG. 13) upon which to push the material roll 602 with roll bumper 610. Lasers, radar, or ultrasonics can also be used to measure distance and position, either in addition to or instead of camera 612.

In an alternate embodiment (not shown), an automated cart is provided. A powered and programmed cart is provided to retrieve material rolls from an initial storage location, and then to return to the material address to be called upon to provide new material rolls to the system. Once emptied of one or more waiting new material rolls, the powered and programmed cart returns to retrieve material rolls from the initial storage location.

FIG. 12 is a perspective view of a gantry crane 500 carrying a material roll 602 used in the present invention, the robotic arm 502 shown in an extended position.

Figure 13:
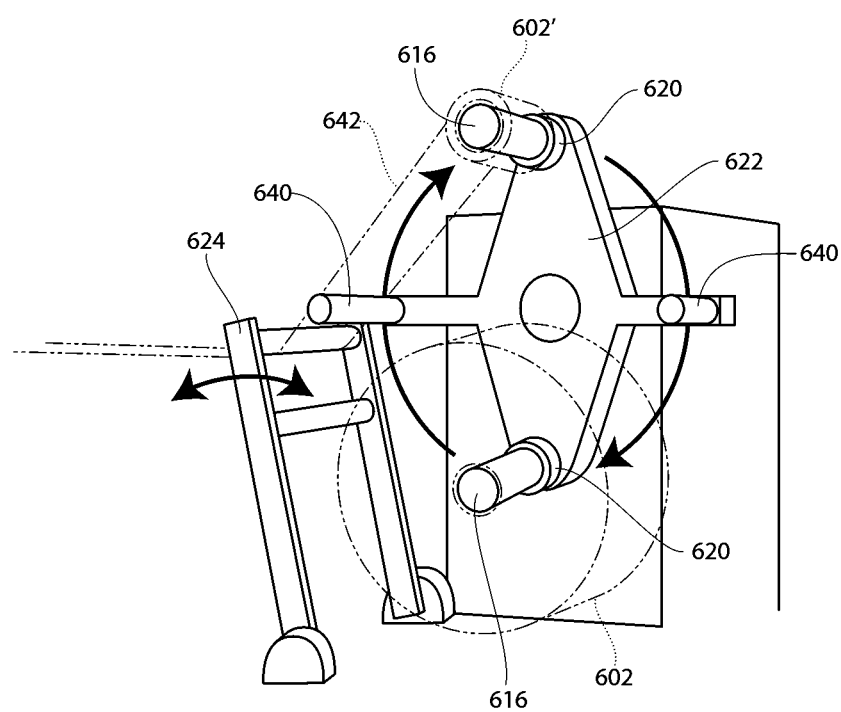
FIG. 13 is a side view of a turret unwind and splicing system for carrying expiring material rolls and waiting new material rolls.

Referring now to FIG. 13, a side view of a turret unwind and splicing system for carrying expiring material rolls 602' and waiting new material rolls 602 is shown. In a preferred embodiment, an expiring material roll 602' is positioned in an expiring material roll position at the top of turret arm 622, and waiting new material rolls 602 are positioned in a waiting roll position at the bottom of turret arm 622. Of course, alternate configurations are possible for the positions of expiring material roll position and the waiting roll position.

Turret unwinds are described for exemplary purposes in U.S. Pat. Nos. 6,701,992, 3,655,143, 3,306,546, 3,460,775, which are incorporated herein by reference.

When the system detects that one of the expiring material rolls 602' in the top position on unwinds 424, 426, 428, 430, 432, 434, and 436 is set to expire of material 642, a splice sequence is initiated between the expiring material roll 602' and the waiting new material roll 602. In a preferable embodiment, a running or expiring roll 602' is at a top position of the turret unwind of FIG. 13, with a waiting new material roll 602 placed by the gantry crane system located at a bottom position of the turret unwind on shaft 616. The web 642 of expiring roll 602' is guided to the hot wire splicer arm 624 structure by a guide roller 640.

Figure 14:
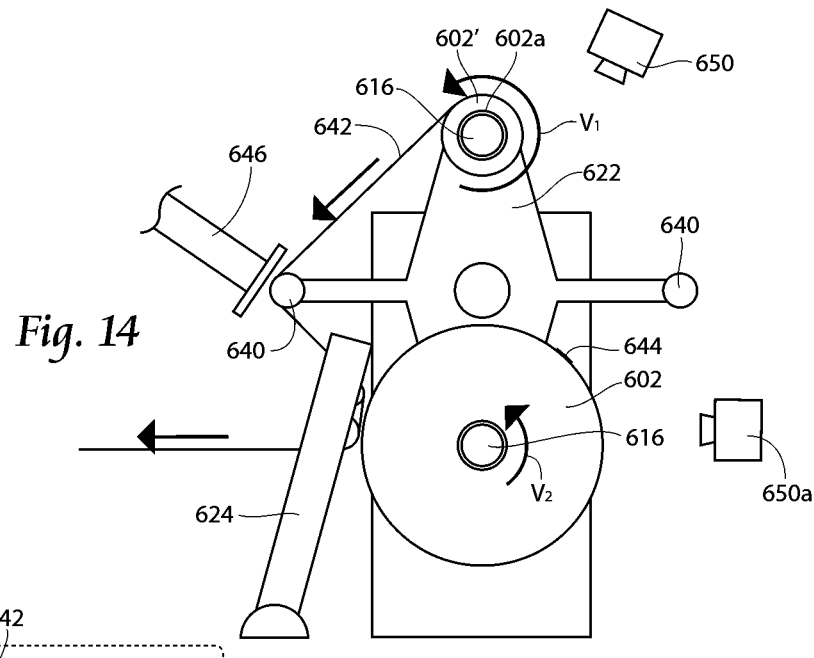
Figure 15:
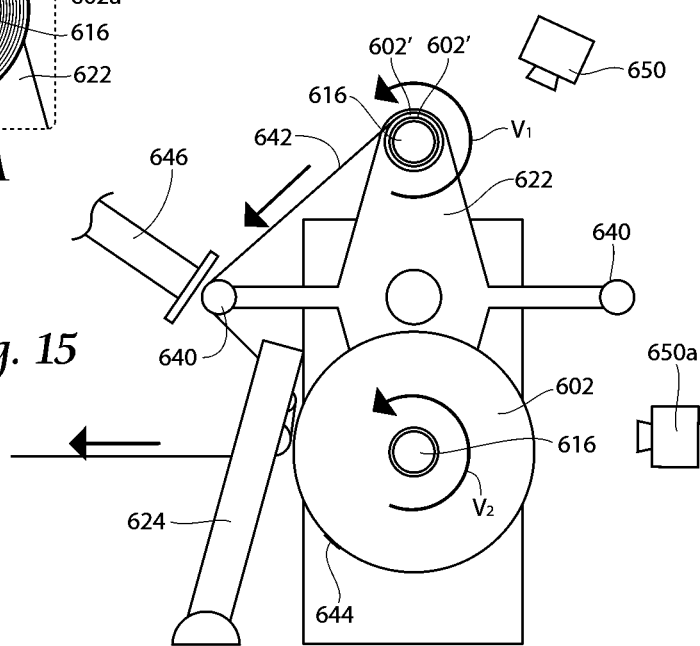

A splice and material recovery sequence is shown with reference to FIGS. 14-22. Referring first to FIGS. 14 and 15, when vision system 650 detects that the expiring roll 602' traveling at velocity V1 is coming close to expiration (compare the size of expiring roll 602' from FIG. 14 to FIG. 15), the waiting new material roll 602 traveling at velocity V2 is driven up to velocity V1.

Figure 14A:
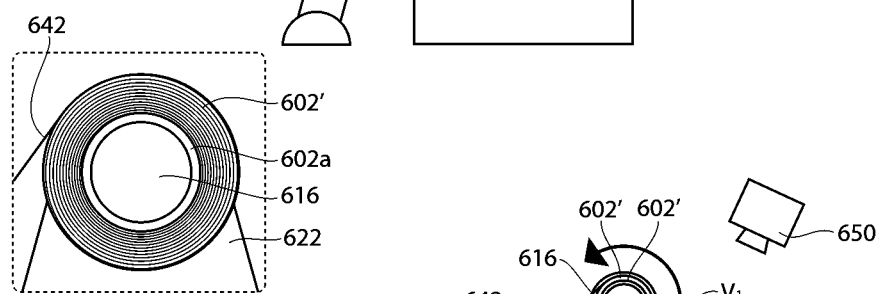

Referring to FIG. 14A, the expiring roll 602' carried by rotating shaft 616 has a core 602a, around which is wrapped material 642.

Figure 16:
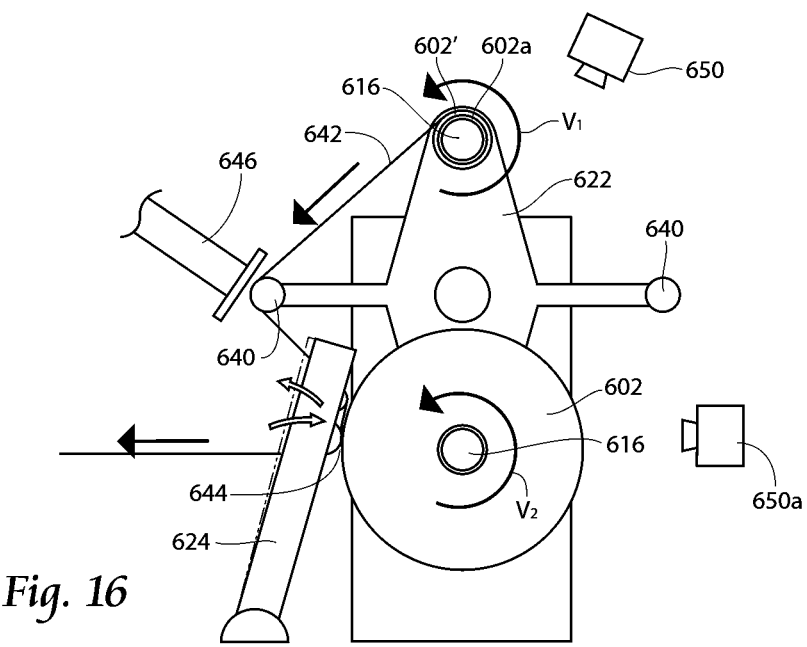

Referring now to FIG. 16, hot wire splicer arm 624 moves in adjacent to the waiting new material roll 602, bringing in the running web 642 into close proximity to the waiting new material roll 602. Vision system 650a (or a photo eye) identifies the location of splice tape 644, and then the waiting new material roll 602 is driven by its controlled motor so that at the moment of splice, a bump of the expiring roll material 642 towards splice tape 644 by arm 624 bonds the expiring roll material 642 to material 644 of the waiting roll 602. A bump arm of the hot wire structure 624 bumps the expiring web 602' to the waiting new material roll, and at the precise moment of contact, splice tape 644 is introduced to splice the web 644 of waiting new material roll 602 and the expiring roll 602' together. At the same time as the bump, the hot wire arm 624 severs the running web with a hot wire. In this manner, the expiring web material 642 is instantly taped to the leading edge of the new roll material 644, as depicted in FIG. 18A.

Figure 17:
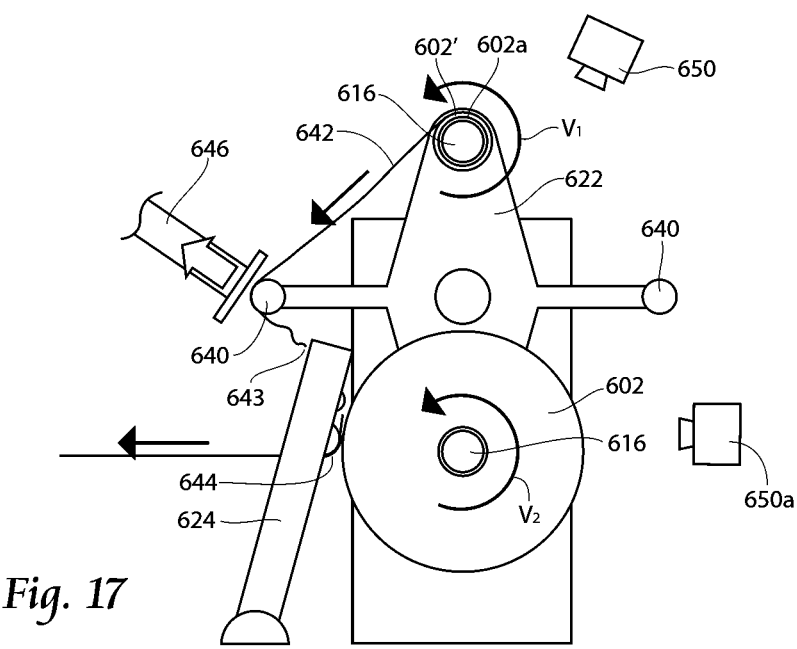

Referring now to FIG. 17, at the moment that the web 642 is severed, a free end 643 of web 642 is created. Just prior to or when web 642 is severed, a vacuum is initiated and drawn by vacuum structure 646 which is coupled to a source of negative pressure (not shown), and the vacuum structure 646 is situated in close proximity to web 642. At this point, web 644 is paid out and is supplied to the process, and there is no longer any use for the expiring roll 602' comprising the web 642 and the core 602a. Material recovery system or vacuum structure 646 recovers free end 643 of web 642, and the remainder of web 642 is paid out by rotation of shaft 616. Web 642 is paid out by shaft 616 until the entirety of the web 642 becomes separated from core 602a as shown in FIG. 19. At this point, point shaft 616 is no longer required to rotate until called upon to begin rotation of the next web of material.

Material recovery system 646 thus automatically separates an expiring roll core 602a from the expiring material 642. Two single material waste streams are created, one of the expiring roll core 602a, and the other of the expiring material 642, which makes recycling and downstream handling of the expiring roll cores 602a and expiring material 642 simpler and more efficient because the waste streams are not required to be handled manually.

Figure 20:
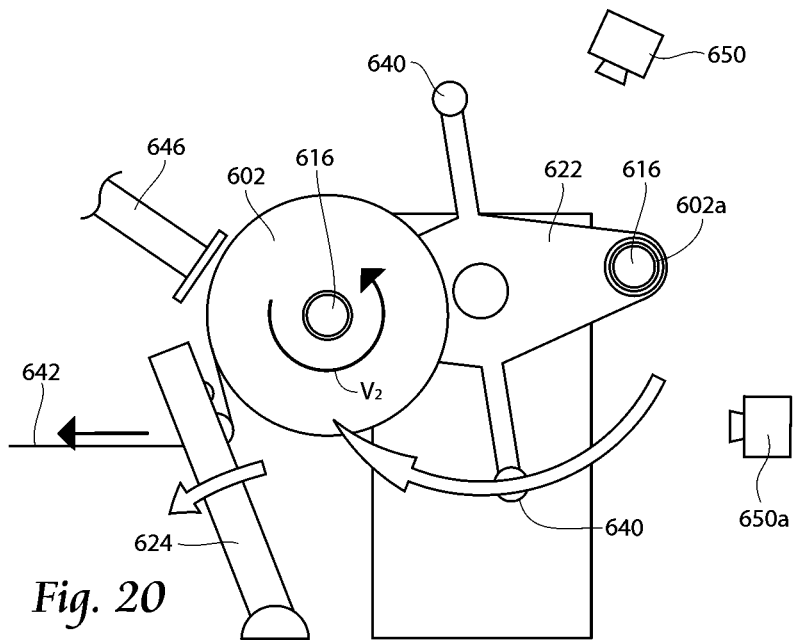

Next referring to FIG. 20, the rotating turret arm 622 rotates clockwise to place the waiting new material roll 602 into the expiring roll position (because the material roll 602 will now be an expiring roll 602'), preferably at the top vertical position of rotating turret arm 622. Clockwise rotation of the turret arm 622 also places the shaft 616 (still carrying core 602a) in the waiting roll position in order to automatically receive a new waiting roll 624. Also at this time, splicer arm 624 swings away. During rotation of the rotating turret arm 622, it is desirable to vary V2 during rotation of the new material roll 602 from the waiting position to the expiring roll position, in order to maintain constant tension and supply rate of web 644 to the downstream processing operations.

Figure 21:
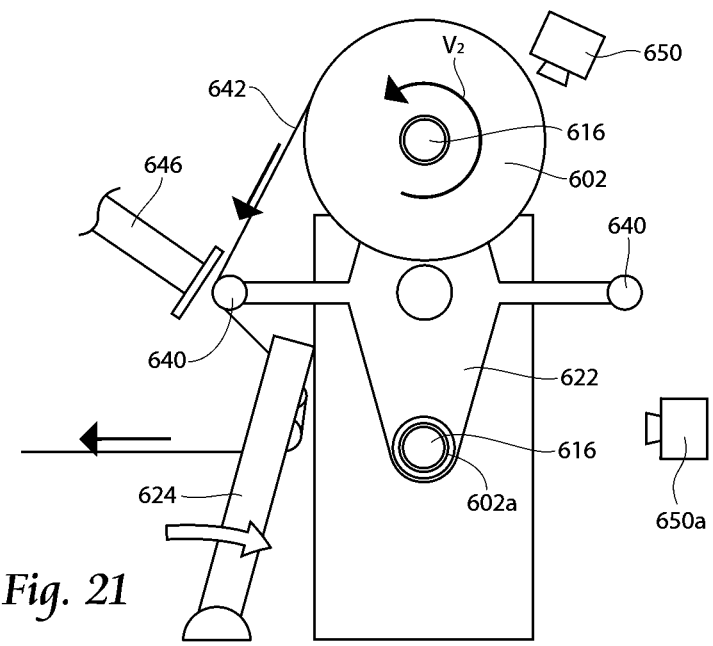

Referring now to FIG. 21, rotating turret arm 622 causes the newly expiring roll 602 to reach the expiring roll position, and eventually splicer arm 624 swings back to its ready position for the next bump sequence.

Figure 22:
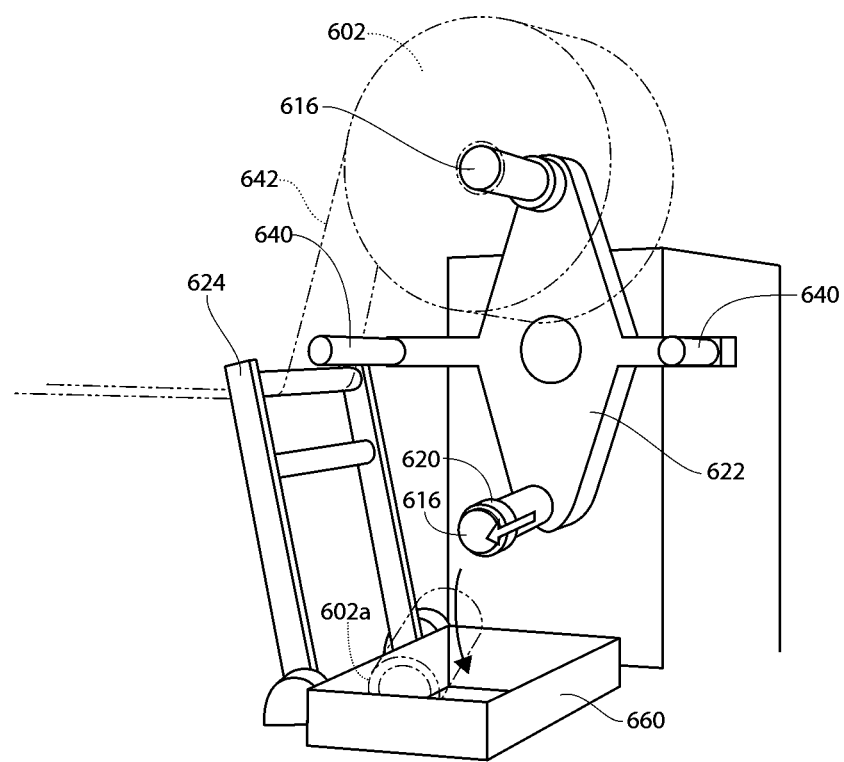

Referring now to FIG. 22, a kicker ring 620 next bumps the core 602a off of shaft 616 for discard, and kicker ring 620 then reverts back to its position proximal to the rotating turret arm 622 to allow shaft 616 to receive the next waiting roll 602, for instance from the unit configured in FIG. 12.

Next, the system demands a replacement waiting new material roll to place upon the shaft 616 at the bottom position of the turret unwind.

At the mezzanine level addresses 404, 406, 408, 410, 412, 414, and 416, magazines of waiting new material roll (FIG. 10) are received from the ground level, and wait for demand. The gantry crane 500 is summoned to pick up a material roll from a cart (FIG. 10) stationed at the dedicated VRC stations, and transport the full material roll to a turret unwind system dedicated to that particular material. The system detects which waiting new material roll requires replacement after its predecessor has been spliced and turned into an expiring roll, and then travels the crane/robot combination 500/502 to the appropriate mezzanine level address 404, 406, 408, 410, 412, 414, and 416, and obtains a replacement waiting new material roll.

The gantry robot is programmed to discard the remainder of the expiring roll (the now empty core 602a) into a waste chute (not shown) on the mezzanine level or to container 660 (FIG. 22), and then to obtain a replacement waiting new material roll from the dedicated VRC from which the appropriate material is located on the cart. When the system detects that all rolls of waiting new material roll are used from a supply cart (FIG. 10), the VRC containing the empty cart is automatically transported to the floor level for replacement of all of the waiting new material rolls.

Figure 23:
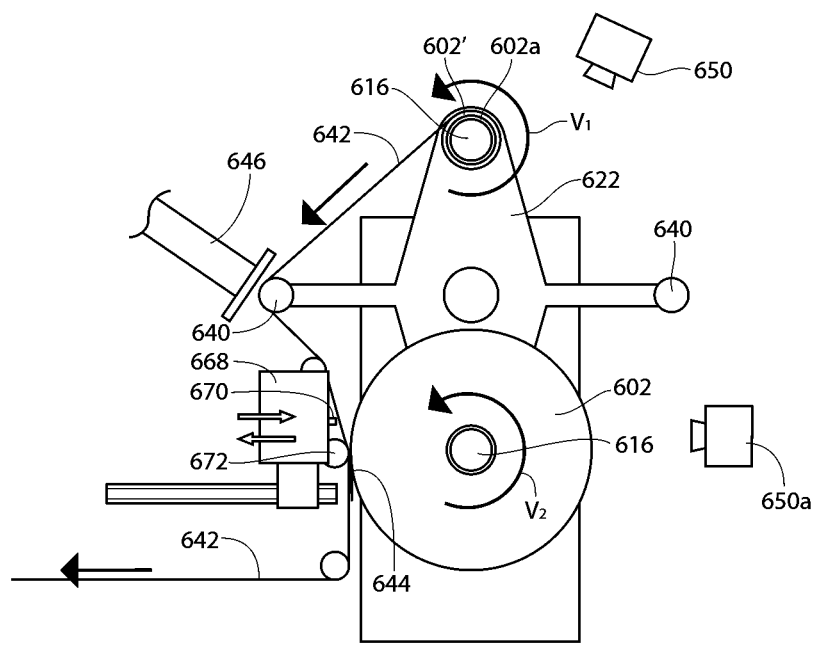
FIG. 23 is a side view of an alternate embodiment of a bump and severing mechanism for bumping an expiring roll to a splice tape on a waiting material roll, and severing the expiring roll.

Referring now to FIG. 23, a side view of an alternate embodiment of a bump and severing mechanism for bumping expiring roll 602' to splice tape 644 on the waiting material roll 602, and severing the expiring roll 602' is shown. In this embodiment, a sliding bump/sever mechanism 668 is engaged when called upon, to bump via roller 672 the expiring web material 642 against splice tape 644. In preferred embodiments, the linear sliding bump/sever mechanism 668 can be fired by an air cylinder, simplifying setup of the pivot arm 624 previously described, or the sliding bump/sever mechanism 668 could be servo motor driven. When called upon, for instance when vision system 650 senses material 602' is running out, the splicing/severing sequence begins. The bump/sever mechanism 668 linearly approaches the web 642 to bump the web 642 into contact with splice tape 644, and momentarily thereafter, a hot wire 670 severs expiring web material 642, allowing newly expiring roll material to be used in the process as shown in FIG. 18a.

Figure 24:
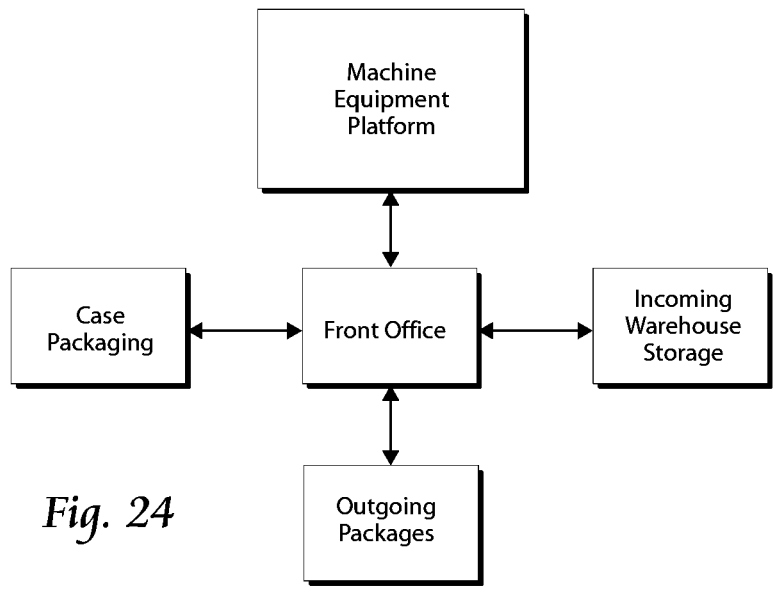
FIG. 24 is a schematic view of a disposable product producing facility, and attendant communications system.

Referring now to FIG. 24, a schematic view of a disposable product producing facility, and attendant communications system is shown. As can be seen, this schematic can be used to plan an inventive production facility of the present invention.

At the conceptual center of the facility is a front office, where communications take place (receiving and sending information) between the front office and a machine equipment platform, an incoming warehouse and storage section, an outgoing packages section, and a case packaging section. The machine equipment platform is where disposable products are produced, e.g., a machine to make diapers. The incoming warehouse/storage section is where raw materials are delivered to the facility, and stored until called upon for introduction into the machine equipment platform or the case packaging platform. The outgoing packages portion of the facility if where formed product in packages and cases, is stored for distribution outside of the facility. The front office will receive information and send information from the different segments to inform of material requirements, inventory, and scheduling.

Figure 25:
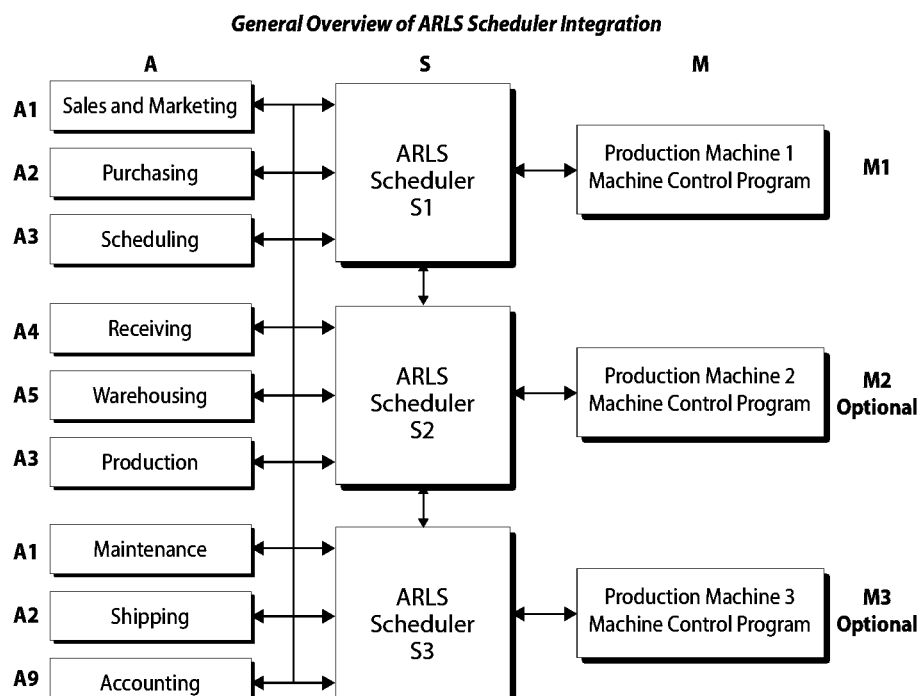
FIG. 25 is a schematic view of a disposable product producing facility with multiple production machines, and attendant communications system.

Referring now to FIG. 25, a schematic view of a disposable product producing facility with multiple production machines, and attendant communications system is shown. Disclosed is an Automatic Roll Loading System (ARLS). A plurality of ARLS schedulers (S1, S2, and S3) for example, communicate with each other, and with their dedicated production machines (Production Machines 1, 2, and 3, respectively). Specifically, the ARLS scheduler(s) of the present invention anticipates when a current run of a product size is coming to an end, and therefore begins loading of material rolls intended for the next product size or code that will be run. Those decisions are informed by, with respect to ARLS scheduler S1 but equally applicable to the schedulers S2 and S3, sales and marketing input/output A1, purchasing input/output A2, and scheduling input/output A3. Sales and marketing input/output A1 contains information related to the desired output quantity of certain disposable products, e.g., SKUs (stock keeping units of a particular product that allows it to be tracked for inventory purposes). A specific material requirement schedule for each of the certain disposable products is necessary, and purchasing input/output A2 reacts with the scheduler S1 to ensure that required materials are on hand at the incoming warehouse storage of FIG. 24. Scheduling input/output A3 reacts with sales and marketing input/output A1, and purchasing input/output A2, as well as the ARLS scheduler S1 to control when ARLS scheduler S1 commands production machine M1 to manufacture a specific product.

ARLS scheduler S1 commands production machine M1 to manufacture a specific product, and when informed by receiving/purchasing/scheduling input/outputs A1/A2/A3 to command machine M1 to manufacture a different specific product, raw material used by production machine M1 may require changeover, e.g., for a size dependent material change such as a chassis web of a different width. Once all material unwinds of machine M1 (e.g., any one of upstairs unwinds of FIG. 9) have the size of material rolls loaded and splices set up, splices can by manually or automatically triggered to splice in the new material rolls and use the running machine process to pull all the new materials through the process. This saves considerable time compared to loading each unwind manually and then manually rethreading each material process throughout the machine. The result is a significant reduction in changeover times and the present technique can be employed for any machine process requiring input of multiple material rolls when different materials (size, weight, color, etc.) are required for different products codes or sizes.

When employing the technique described herein, splicing in different width materials and pulling them through a running machine process will not result in the immediate making of acceptable products. The present method results in intentionally pulling in material widths different than what the current product code being run is setup for, so certain details will result in unacceptable product; for instance, glue applicator patterns may exceed the new material width and therefore glue applicators are turned off for the duration of this material pull through technique. For the same reason, web with detectors are temporarily disable or ignored, and web guides put into a non-responsive mode so they do not try and respond to material widths not compatible with their current setup. Those machine capabilities are restored prior to starting the next good product run, but by pulling in new materials through web processes by using the old materials already threaded through web processes, good-product to good-product changeover is greatly sped.

An ARLS Scheduler monitors machine speed, consumption of raw materials, materials remaining on each turret unwind, progress on case count of current product code run, schedule of next product code run, materials available at machine, materials remaining on each material loading cart, and optionally, materials in warehouse, and general position of robot carts in motion.

Figure 26:
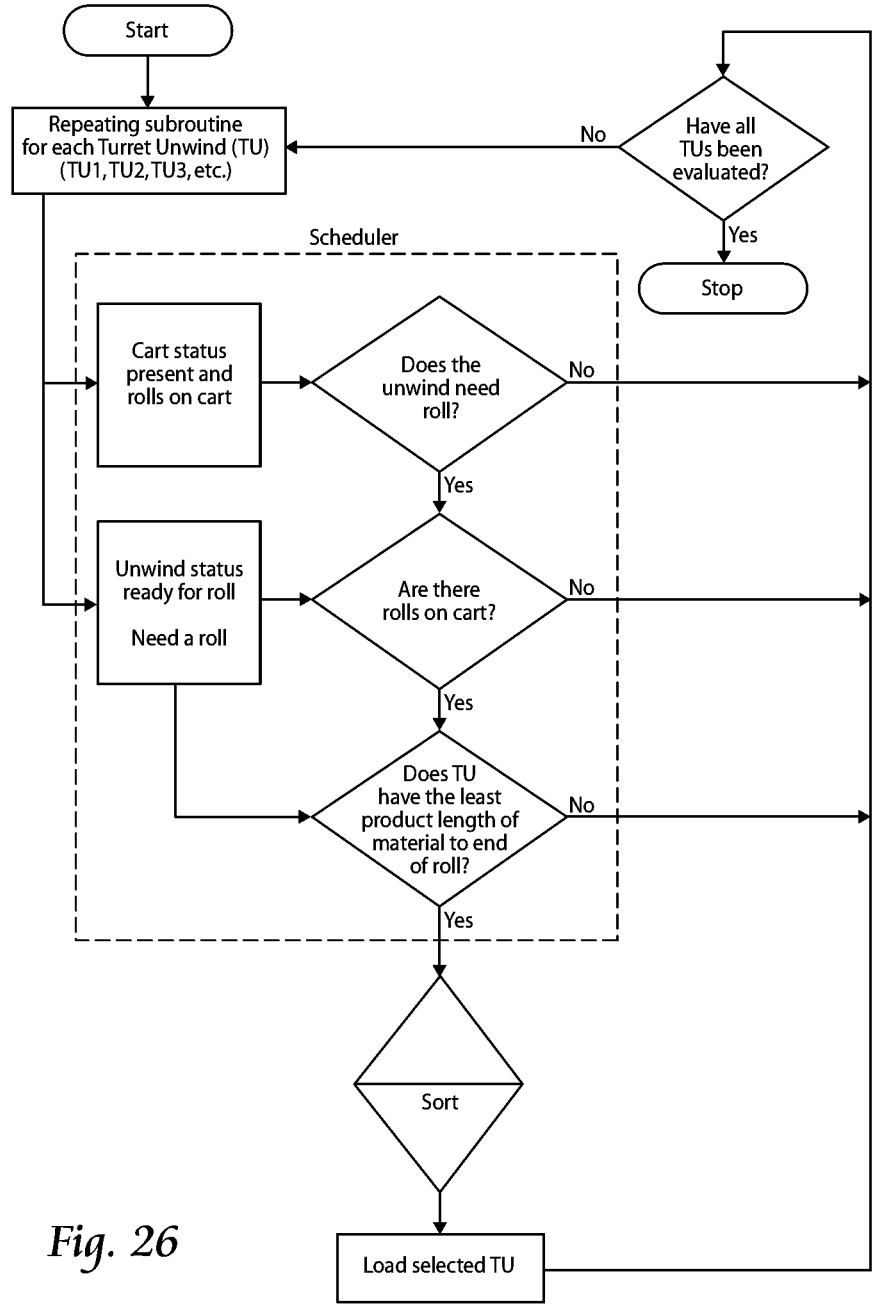
FIG. 26 is a decision tree for material supply.

Referring now to FIG. 26, a decision tree for material supply is shown. First, the ARLS Scheduler determines which turret unwind should be loaded next. It also determines when material rolls specific to the NEXT product code to be run should be loaded onto the associated turret unwinds. This is part of the preparation to conduct the special splice event as part of the current product code run shutdown. Once new materials are pulled through the machine process (auto-threaded) by the expiring materials, the machine can be fully shut down in preparation for other, non-material related changeover activities to set the machine up for the next product code run.

The ARLS Scheduler may also keep track of the changeover parts, assemblies, and set-ups needed for each specific changeover to assist the machine operators and technicians in their outside time preparations for the changeover as well as during the inside time changeover activities when in progress.

The basic roll loading decision is informed by information queries such as: material remaining on each cart; status of a turret unwind as ready to load; and the time remaining or product pitches remaining to end of roll on the turret unwind. The decision could be located in the turret unwind control routine, the ARLS PLC, or the machine control PLC depending on size, complexity, or configuration of machine.

As described with respect to FIGS. 1-23, a vertical reciprocating conveyor or a robot is used to carry waiting new material rolls from a main processing level to the material unwinding level. A robotic assembly obtains an expiring roll and discards the roll in a waste chute. Once on the material unwinding level, the waiting new material rolls are staged at a material address dedicated to that particular material. A robotic assembly acquires a material roll from one of said material addresses and transports and places the material roll onto its appropriate auto-fed material unwinding system.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A system for manufacturing disposable products, the system comprising:
    a production machine having a production floor for producing each of a first configuration of disposable products and a second configuration of disposable products, the first configuration of disposable products produced from material rolls of a first set of material rolls and the second configuration of disposable products produced from material rolls of a second set of material rolls;
    a controller communicatively coupled to the production machine, the controller programmed to:
        generate an output signal controlling whether the first configuration or the second configuration of disposable products is produced by the production machine, the output signal generated responsive to a plurality of input signals received by the controller;
        control a roll transfer device of the production machine to selectively couple at least one of a first material roll of the first set of material rolls and a second material roll of the second set of material rolls with the production machine based upon at least one of the input and output signals, so as to enable the production machine to selectively produce the first or the second configuration of disposable products.

2. The system of claim 1, wherein the input signals comprise at least one of scheduling input, sales and marketing input, purchasing input, receiving input, warehousing input, production input, maintenance input, shipping input, and accounting input.

3. The system of claim 1, wherein the production machine comprises turret unwind systems onto which the first material roll and the second material roll are loaded.

4. The system of claim 3, wherein the roll transfer device comprises a gantry crane system and a robotic arm configured to selectively transfer the first material roll and the second material roll to the turret unwind systems.

5. The system of claim 1, wherein the controller is programmed to switch operation of the production machine between a first operational mode that produces the first configuration of disposable products and a second operational mode that produces the second configuration of disposable products; and
wherein, when the production machine is switched from the first operational mode to the second operational mode, the controller is programmed to:
receive additional inputs comprising an input of machine speed, an input of consumption of raw material, and an input of material remaining on one of the turret unwind systems having a material roll of the first set of material rolls coupled thereto;
anticipate when a current run of the first configuration of disposable products is ending based upon the inputs; and
control the roll transfer device to couple the second material roll to another of the turret unwind systems based on the anticipated ending of the first configuration of disposable products.

6. The system of claim 5 wherein the second material roll is located at a designated address, and wherein the controller is programmed to cause the roll transfer device to retrieve the second material roll from the designated address at a time associated with the anticipated ending of the first configuration of disposable products.

7. The system of claim 1, wherein the controller controls the turret unwind systems of the production machine to automatically splice the second material roll to a material roll of the first set of material rolls currently in use by the production machine.

8. The system of claim 7, wherein the material rolls of the first set of material rolls and the material rolls of the second set of material rolls have a same material thereon.

9. The system of claim 7, wherein material rolls of the first set of material rolls have a first roll width and the material rolls of the second set of material rolls have a second roll width, the second roll width larger than the first roll width.

10. The system of claim 9, wherein the controller causes the production machine to continue running after splicing of the second material roll to the material roll of the first set of material rolls currently in use, having the different material widths, such that all material of the material roll of the first set of material rolls currently in use is pulled through the production machine.

11. The system of claim 10, wherein the controller deactivates one or more components of the production machine during the pull through of the material of the material roll of the first set of material rolls currently in use and reactivates the one or more components prior to starting a production run of the second configuration of disposable products.

12. The system of claim 11, wherein the one or more components comprises at least one of an adhesive applicator, web defect detectors, and web guides.

13. The system of claim 1 wherein the production machine is located on a ground level and the roll transfer device and turret unwind systems are located on a mezzanine level positioned over the production machine.

14. A controller-based method for manufacturing disposable products via a system including a production machine, the method comprising:
receiving input signals at a controller communicatively coupled to the production machine;
determining, based on the input signals, an operational mode of the production machine to produce either a first configuration of disposable products or a second configuration of disposable products;
based on the determined operational mode of the production machine, selecting use of a first set of material rolls configured to produce the first configuration of disposable products or use of a second set of material rolls configured to produce the second configuration of disposable products;
identifying a time when the selected one of the first set of material rolls and the second set of material rolls is to be loaded onto turret unwinds of the production machine;
causing a roll transfer device of the production machine to load the selected one of the first set of material rolls and the second set of material rolls onto the turret unwinds at the identified time, so as to enable production of the first configuration of disposable products or the second configuration of disposable products by the production machine;
controlling the turret unwinds of the production machine to automatically splice material rolls of the first set of material rolls or the second set of material rolls with existing material rolls currently in use by the production machine;
causing the production machine to continue running after splicing of the material rolls of the first set of material rolls or the second set of material rolls with the existing material rolls until an entirety of materials on the existing material rolls is pulled through the production machine; and
deactivating one or more components of the production machine during the pull through of the materials on the existing material rolls.

15. The method of claim 14 further comprising deactivating at least one of an adhesive applicator, web defect detectors, and web guides during the pull through of the materials on the existing material rolls.

16. The method of claim 14 wherein the one or more components of the production machine are deactivated when a material width of at least one of the material rolls of the first set of material rolls or at least one of the second set of material rolls is different from a material width of the existing material rolls.

17. A controller-based method for manufacturing disposable products via a system including a production machine, the method comprising:
operating the production machine according to a first operational mode to produce a first configuration of disposable products, the first configuration of disposable products produced from a first material roll coupled to a first turret unwind system; and
switching operation of the production machine to a second operational mode to produce a second configuration of disposable products, the second configuration of disposable products produced from a second material roll, where a web of material on the second material roll has a different width from a web of material on the first material roll;

wherein, in switching operation of the production machine to the second operational mode, the method comprises:

controlling a roll transfer device to selectively transport and couple the second material roll to a second turret unwind system of the production machine;

controlling the turret unwind system of the production machine to splice the second material roll with the first material roll currently in use by the production machine; and operating the production machine to continue miming after splicing of the second material roll with the first material roll until an entirety of the web of material on the first material roll is pulled through the production machine.

18. The method of claim 17 wherein, in switching operation of the production machine to the second operational mode, the method further comprises:

identifying, via a scheduler of the system, when operation of the production machine according to the first operational mode is to end, based on a plurality of input signals received by the scheduler; and controlling the roll transfer device and the second turret unwind system to automatically provide the second material roll and to splice the second material roll to the first material roll, respectively, based on the identified ending of the operation of the production machine according to the first operational mode.

19. The method of claim 18 wherein the input signals comprise at least one of scheduling input, sales and marketing input, purchasing input, receiving input, warehousing input, production input, maintenance input, shipping input, and accounting input.

20. The method of claim 17 further comprising controlling a gantry crane system and a robotic arm to selectively transfer the second material roll to the second turret unwind system.

21. The method of claim 17 wherein, in switching operation of the production machine to the second operational mode, the method further comprises deactivating one or more components of the production machine during the pull through of the of the web of material on the first material roll.

* * * * *

UNITED STATES PATENT AND TRADEMARK OFFICE
CERTIFICATE OF CORRECTION

PATENT NO. : 11,325,801 B2
APPLICATION NO. : 16/947963
DATED : May 10, 2022
INVENTOR(S) : Follen et al.

Page 1 of 1

It is certified that error appears in the above-identified patent and that said Letters Patent is hereby corrected as shown below:

On the Title Page

Page 2, item [56], Column 2, under "U.S. PATENT DOCUMENTS", Line 13, for ref. US7214174, delete "Mien et al." and insert -- Allen et al. --, therefor.

Page 2, item [56], Column 2, under "U.S. PATENT DOCUMENTS", Line 15, for ref. US7441579, delete "Mami" and insert -- Adami --, therefor.

In the Claims

Column 19, Claim 11, Line 59, delete "of the material of the material" and insert -- of the material --, therefor.

Column 21, Claim 17, Line 11, delete "miming" and insert -- running --, therefor.

Column 22, Claim 21, Line 20, delete "of the of the" and insert -- of the --, therefor.

Signed and Sealed this
Twenty-sixth Day of July, 2022

Katherine Kelly Vidal
*Director of the United States Patent and Trademark Office*